United States Patent
Abraham et al.

(10) Patent No.: US 6,624,140 B1
(45) Date of Patent: Sep. 23, 2003

(54) SYNTHETIC PEPTIDES WITH ANTIMICROBIAL AND ENDOTOXIN NEUTRALIZING PROPERTIES FOR MANAGEMENT OF THE SEPSIS SYNDROME

(75) Inventors: Philip Richard Abraham, Duivendrecht (NL); Bernard Jan Appelmelk, Amsterdam (NL); Sander Jan Hendrik Van Deventer, Haarlem (NL)

(73) Assignee: Academisch Ziekenhuis Bij de Universiteit van Amsterdam Academisch Medisch Centrum, Amsterdam-Zuidoost (NL)

( * ) Notice: Subject to any disclaimer, the term of this patent is extended or adjusted under 35 U.S.C. 154(b) by 0 days.

(21) Appl. No.: 09/493,211

(22) Filed: Jan. 28, 2000

Related U.S. Application Data

(63) Continuation-in-part of application No. PCT/NL97/00449, filed on Jul. 31, 1997.

(51) Int. Cl.[7] .......................... A01N 37/18; A61K 38/00
(52) U.S. Cl. ................. 514/2; 514/12; 514/13; 514/14; 530/300; 530/324; 530/325; 530/326; 530/344; 435/252.1; 435/252.33; 435/253.1; 435/253.4; 435/254.1
(58) Field of Search .................. 514/2, 12, 13, 514/14; 530/300, 324, 325, 326, 344; 435/252.1, 252.33, 254.1, 253.1, 253.4

(56) References Cited

FOREIGN PATENT DOCUMENTS

| WO | WO93/05802 | 4/1993 |
|----|------------|--------|
| WO | WO93/14115 | 7/1993 |
| WO | WO94/20532 | 9/1994 |
| WO | WO95/05393 | 2/1995 |

OTHER PUBLICATIONS

Cantor et al., Biophysical Chemistry Part I: The Conformation of Biological macromolecules, Chapter 5, pp. 298–305 (1980).*

"Design of Active analogues of a 15–Residue Peptide Using D–Optimal Design, QSAR and a Combinatorial Search Algorithm" by Mee et al, Jan. 1997, vol. 49, No. 1.

"Reciprocal Effects of Apolipoprotein and Lytic Peptide Analogs on Membranes" by Tytler et al, vol. 268, No. 29, Oct. 1993.

* cited by examiner

Primary Examiner—Christopher S. F. Low
Assistant Examiner—Chih-Min Kam
(74) Attorney, Agent, or Firm—Sughrue Mion, PLLC

(57) ABSTRACT

A peptide with an amino acid composition such that the peptide is amphipathic, cationic and forms a stable α-helix and has the following structure comprising at least 12 amino acids $R_1\text{-}R_2\text{-}A_1\text{-}B_1\text{-}(A_2\text{-}B_2\text{-}C_1\text{-}A_3)_m\text{-}(C_2)_n\text{-}R_3$, wherein A=an amino acid selected from the basic amino acids Lys,Arg or His
B=an amino acid selected from the aromatic amino acids Phe, Trp or Tyr
C=an amino acid selected from the group comprising the hydrophobic amino acids Leu, Ile, Val or Ala, and
said peptide has either the orientation according to the formula or the retro orientation thereof, wherein at least 0-m of the repetitive sequence motifs $(A_2\text{-}B_2\text{-}C_1\text{-}A_3)$ have the retro orientation and the remaining repetitive motifs $(A_2\text{-}B_2\text{-}C_1\text{-}A_3)$ have the orientation as presented in the formula and wherein, $R_1\text{-}R_2\text{-}$ and $R_3$ are a number of amino acids, and wherein m=1–10, preferably 2–8, more preferably 2–5 and
n=1–3, a pharmaceutical composition comprising such a peptide application thereof in treatment or diagnosis related to i.a. parasite infection topical and systemic tumors and septic shock.

36 Claims, 14 Drawing Sheets

A

B

A

B

B

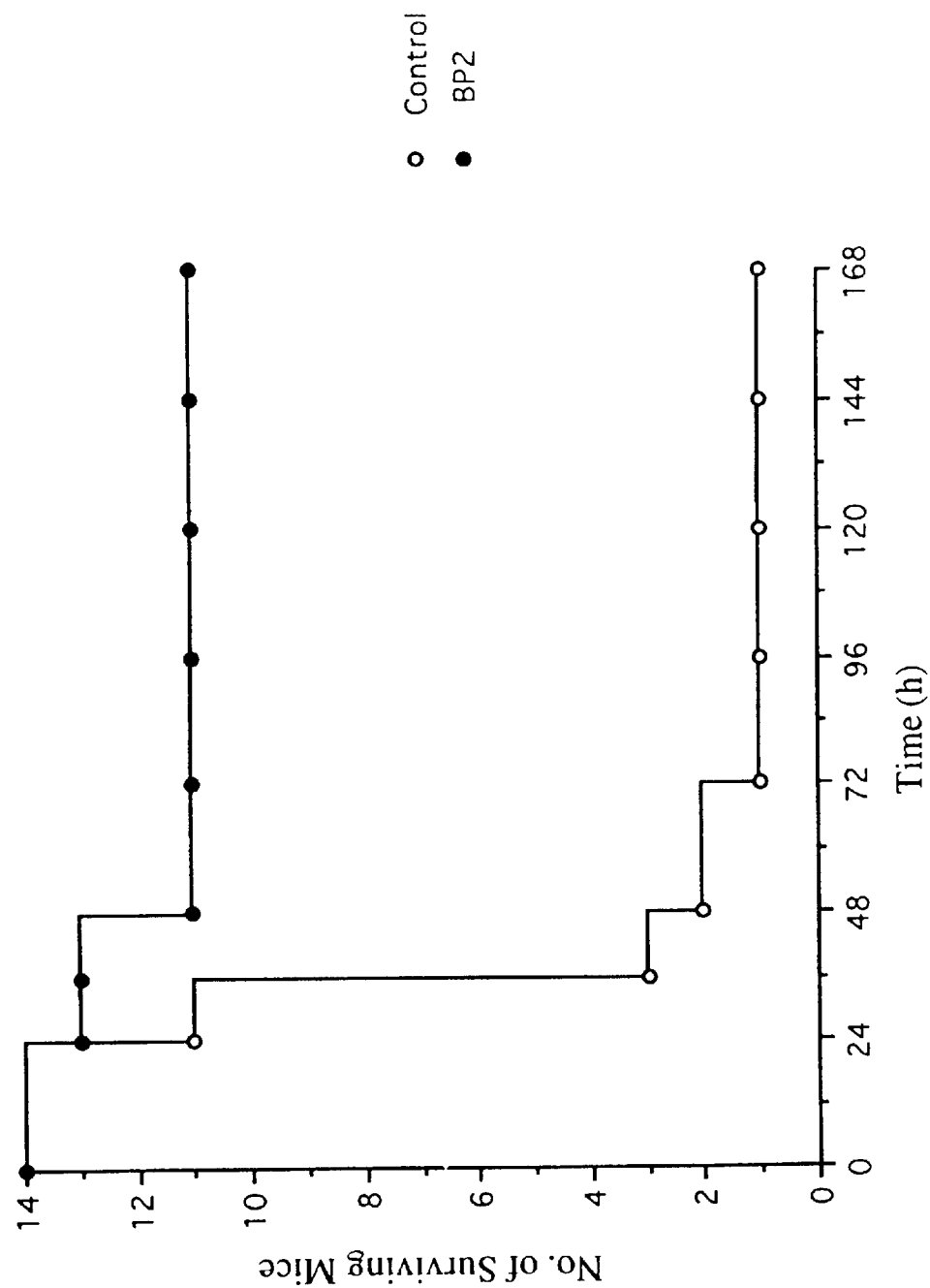

SEQUENCE LISTING

<160> NUMBER OF SEQ ID NOS:   9

<210> SEQ ID NO 1
<211> LENGTH: 19
<212> TYPE: PRT
<213> ORGANISM: Artificial
<220> FEATURE:
<223> OTHER INFORMATION: Synthetic peptide

<400> SEQUENCE: 1

Gly Arg Leu Arg Lys Lys Trp Lys Ala Phe Lys Lys Phe Leu Lys Ile
1               5                   10                  15

Leu Ala Cys

<210> SEQ ID NO 2
<211> LENGTH: 19
<212> TYPE: PRT
<213> ORGANISM: Artificial
<220> FEATURE:
<223> OTHER INFORMATION: Synthetic peptide

<400> SEQUENCE: 2

Gly Lys Trp Lys Leu Phe Lys Lys Ala Phe Lys Lys Phe Leu Lys Ile
1               5                   10                  15

Leu Ala Cys

<210> SEQ ID NO 3
<211> LENGTH: 19
<212> TYPE: PRT
<213> ORGANISM: Artificial

```
<220> FEATURE:
<223> OTHER INFORMATION: Synthetic peptide

<400> SEQUENCE: 3

Gly Lys Trp Lys Ala Phe Lys Lys Ala Phe Lys Lys Phe Ala Lys Ile
1               5                   10                  15

Leu Ala Gly

<210> SEQ ID NO 4
<211> LENGTH: 19
<212> TYPE: PRT
<213> ORGANISM: Artificial
<220> FEATURE:
<223> OTHER INFORMATION: Synthetic peptide

<400> SEQUENCE: 4

Gly Lys Trp Lys Leu Phe Lys Lys Ala Phe Lys Lys Phe Leu Lys Ile
1               5                   10                  15

Leu Ala Gly

<210> SEQ ID NO 5
<211> LENGTH: 29
<212> TYPE: PRT
<213> ORGANISM: Artificial
<220> FEATURE:
<223> OTHER INFORMATION: Synthetic peptide

<400> SEQUENCE: 5

Cys Gly Gly Gly Gly Gly Gly Gly Gly Lys Trp Lys Ala Phe Lys
1               5                   10                  15

Lys Ala Phe Lys Lys Phe Ala Lys Ile Leu Ala Cys Gly
                20                  25

<210> SEQ ID NO 6
<211> LENGTH: 18
<212> TYPE: PRT
<213> ORGANISM: Artificial
<220> FEATURE:
<223> OTHER INFORMATION: Synthetic peptide

<400> SEQUENCE: 6

Gly Lys Leu Lys Lys Lys Trp Lys Ala Ala Lys Lys Phe Leu Lys Lys
1               5                   10                  15

Cys Ser

<210> SEQ ID NO 7
<211> LENGTH: 18
<212> TYPE: PRT
<213> ORGANISM: Artificial
<220> FEATURE:
<223> OTHER INFORMATION: Synthetic peptide

<400> SEQUENCE: 7

Gly Lys Trp Lys Leu Phe Lys Lys Ala Ala Lys Lys Phe Leu Lys Lys
1               5                   10                  15

Cys Ser

<210> SEQ ID NO 8
<211> LENGTH: 18
<212> TYPE: PRT
<213> ORGANISM: Artificial
<220> FEATURE:
<223> OTHER INFORMATION: Synthetic peptide
```

-continued

```
<400> SEQUENCE: 8

Gly Lys Trp Lys Ala Phe Lys Lys Ala Ala Lys Lys Phe Ala Lys Lys
1               5                   10                  15

Cys Ser

<210> SEQ ID NO 9
<211> LENGTH: 19
<212> TYPE: PRT
<213> ORGANISM: Homo sapiens

<400> SEQUENCE: 9

Ile Lys Ile Ser Gly Lys Trp Lys Ala Gln Lys Arg Phe Leu Lys Met
1               5                   10                  15

Ser Gly Cys
```

SYNTHETIC PEPTIDES WITH ANTIMICROBIAL AND ENDOTOXIN NEUTRALIZING PROPERTIES FOR MANAGEMENT OF THE SEPSIS SYNDROME

This application is a Continuation-in-Part of PCT/NL97/00449 filed Jul. 31, 1997.

BACKGROUND OF THE INVENTION

Bacterial infections as a complication of surgery, prolonged hospitalization, accidents and other traumatic events, may lead to serious clinical symptoms such as sepsis, septic shock, inadequate organ perfusion, multiple organ failure and acute respiratory distress syndrome (ARDS). Despite advances in medicine over the past decade, an increase in the incidence of sepsis is evident with a mortality rate of 20 to 80%. The sepsis syndrome is initiated when microorganisms bypass the natural defensive barriers of the body, such as skin and mucous membranes. If the immune system is unable to arrest the infection locally, the organism or its toxins may invade the circulation, where specific bacterial products elicit an inflammatory response that leads to the activation of an array of plasma proteins and cellular defense systems. Although mobilisation of the defence systems of the host is of paramount importance in combatting invading organisms, a cascade of events may simultaneously be triggered that can lead to irreversible tissue injury and organ dysfunction. Uncontrolled infections with Gram-negative bacteria such as *Escherichia coli*, Klebsiella spp., Neisseria spp., *Pseudomonas aeruginosa*, Salmonella spp, or Bordella spp. or the Gram-positive bacteria *Staphylococcus aureus*, Enterococcus spp., Streptococcus spp., *Micrococcus luteus* or *Listeria monocytogenes* give rise to a variety of clinical symptoms collectively referred to as the sepsis syndrome. The component of Gram-negative bacteria responsible for the initiation of the host response is termed endotoxin or lipopolysaccharide (LPS), a major glycolipid constituent of the outer membrane. In the circulation, LPS stimulates specific blood cells to produce endogenous mediators of inflammation termed cytokines such as tumor necrosis factor alpha (TNF-$\alpha$), interleukin-6 (IL-6) and interleukin-8 (IL-8) which have profound physiological effects on the organs and blood vessels of the body. Persistent stimulation of the cellular defence system by excessive LPS leads to overproduction of cytokines which activate a cascade of secondary inflammatory mediators eventually leading to blood vessel damage, circulatory and metabolic disturbances. The toxic component of the LPS molecule is the highly conserved Lipid A moiety which is sufficient to induce the pathophysiological changes characteristic of sepsis.

The prognosis of patients with endotoxemia would be considerably improved if the onset of sepsis could be detected at a sufficiently early stage in the disease process to enable effective treatment. Direct measurement of circulating endotoxins is of importance for the prediction of important clinical events such as bacteremia, septic shock and death. Clinically significant endotoxemia may go undetected by the currently available endotoxin assay, the Limulus amoebocyte lysate assay or LAL test, which has been shown to have serious limitations relating to sensitivity as well as to interference by plasma factors.

Current therapeutic options for Gram-negative bacterial sepsis are limited to anti microbial agents, hemodynamic support and management of sepsis-induced organ dysfunction. Although conventional antibiotic therapy is effective in halting the proliferation of susceptible micro-organisms, the massive release of LPS into the circulation by damaged bacteria may aggravate a septic episode. The relative importance of endotoxin release (endotoxemia) versus bacterial proliferation (bacteremia) during Gram-negative septic shock, however, has not fully been defined. Extensive clinical use of conventional antibiotics such as penicillins, cephalosporins and the like, in the treatment of bacterial infections during the past three decades, has resulted in a dramatic reduction in the efficacy of antibiotic therapy due to an alarming increase in the number of multi-drug-resistant bacteria.

Efforts to intervene directly in the pathophysiological mechanisms which underlie the septic process have yielded inconsistent and largely disappointing results. Antiendotoxin monoclonal antibodies, anti-cytokine therapies and other anti-inflammatory strategies have proven not to be of sufficient benefit to warrant approval as standard adjunctive therapies for human sepsis. Because of the central role of LPS in the development of the sepsis syndrome, therapies designed to enhance the clearance or to neutralise the detrimental effects of endotoxin may prove beneficial. Therapy targeting the initial interactions of LPS is likely to be of most benefit when administered either early in the pathogenesis before widespread vascular injuries have taken place or prophylactically to high risk patients. However, since it is important to prevent further activation of inflammatory cells during the course of bacterial sepsis there may be a role for such treatment even after septic shock has become established. Characteristics of an anti-endotoxin reagent that would be desirable for therapeutic application include specific and avid binding to LPS concomitant with LPS-neutralizing activity, inherent systemic stability and low cytotoxicity.

A clinical syndrome indistinguishable from Gramnegative septic shock via the same endogenous mediators of inflammation in the absence of endotoxemia may be initiated by Gram-positive bacteria. In this instance, the initiation of the host response has been attributed to lipoteichoic acid (LTA), a major constituent of the outer membrane of Gram-positive bacteria. An additional cell-wall component common to both Gram-negative and Gram-positive bacteria that has been shown to induce cytokines in vitro, is the peptidoglycan and/or naturally occurring breakdown products of this macromolecular structure. Although LPS and LTA share few common structural features, one common physical property of these molecules is amphipathicity, a consequence of a specific orientation of negatively charged hydrophilic groups and hydrophobic side chains of longchain fatty acid residues. On the basis of recent experimental evidence, a number of common steps in the pathway of cytokine induction by these toxic bacterial cell-wall components has been proposed.

Anti-microbial peptides are generally induced in animals in response to injury and infection. The synthesis of these factors of the innate or non-adaptive immune system may be induced by a variety of stimuli including Grain-positive and Gram-negative bacteria, fungi and viruses. Animal peptide antibiotics are generally small linear or cyclic basically charged molecules such as cecropins and defensins from mammalian and insect cells, magainin from frog skin, melittin from bee venom and tachyplesins from the horseshoe crab hemolymph which act on a rather broad spectrum of microbial organisms that often belong to the natural flora associated with the animal. The antibacterial activity of the linear class of cationic peptide antibiotics has been found to be dependent on the ability to form $\alpha$-helical structures which are capable of disrupting the integrity of the bacterial outer membrane (OM) by the formation of ion-channels in the lipid bilayer due to self-aggregation of peptide monomers in which the hydrophilic amino acid residues are oriented towards the interior of the membrane pore and the hydrophobic residues at the exterior interacting with phospholipid groups of the cell wall. The molecular basis of the integrity of the OM resides in the electrostatic linkage between the negatively charged Lipid A components of adjacent LPS molecules and divalent cations such as $Mg^{2+}$ and $Ca^{2+}$. Disruption of the cross-linkages, by displacement of these cations with positively charged entities of high affinity for LPS, was postulated to result in membrane destabilization. However, previous studies have also indicated that cationicity of an anti-microbial peptide alone is not the sole determinant for OM-permeabilizing activity, but that a specific configuration is essential for high affinity binding to LPS. In addition, since the Lipid A moiety of LPS is not easily accessible from the periphery of the cell by virtue of being submerged in the membrane, a further requirement of an effective LPS ligand could be small size for effective membrane penetration.

A number of naturally occurring proteins and polypeptides have been reported to bind and neutralize LPS. These include polymyxin B (PmB), Limulus-anti-LPS factor (LALF), the human neutrophil-derived CAP18 and bactericidal/permeability-increasing protein (BPI). PmB and LALF detoxify LPS in vitro and afford protection against endotoxin-mediated lethality in experimental animals, but toxicity precludes their clinical use against Gram-negative bacterial infections. The CAP18 protein inhibits LPS responses in vitro but currently available data are not sufficient for assessment as a potential therapeutic agent in the treatment of sepsis. Limitations to the therapeutic utility of the BPI protein or the truncated recombinant derivatives $rBPI_{23}$ or $rBPI_{21}$ in clinical endotoxic shock, are the rapid clearance from the circulation and lowered efficacy against complex endotoxins. Synthetic peptide derivatives incorporating the potential LPS-binding domains of LALF, CAP18 or BPI have all shown unfavourable properties such as diminished anti-microbial activity and lowered affinity for Lipid A with respect to the parent molecules.

DESCRIPTION OF THE INVENTION

The applicants have derived a new generation of LPS-binding peptides termed bactericidal peptides (BP) by means of molecular modelling and rational design techniques. General properties included in the design of the peptides were restricted size, unique conformational and chemical characteristics, solubility and low cytoxicity. Specific characteristics included in the structure of the peptides were the presence of multiple sequence elements constituting potential LPS-binding domains presented in a specific conformation for optimal binding (high avidity) to the lipid A component of LPS. The peptides can be synthesized by solid-state chemistry with Fmoc (9-fluorenylmethoxy-carbonyl) amino acid derivatives, purified to homogeneity by reverse-phase high-pressure liquid chromatography and verified by analytical HPLC, amino acid analysis and mass-spectrometry in a manner known per se. Any known methodology of peptide synthesis can be applied and is readily available to a person skilled in the art.

CHARACTERISTICS OF THE INVENTION

Biochemical and biological characterisation of the synthetic peptides or biotinylated derivatives demonstrated:

1) Potent anti-microbial activities against Gram-negative as well as Gram-positive bacteria
2) The ability to bind specifically to the Lipid A components of heterologous endotoxins with high affinity relative to Polymyxin B, an established high affinity endotoxin binder.
3) The ability to complex with and precipitate LPS from solution.
4) The ability to detect endotoxin concentrations of <0.1 pg/ml in diluted plasma.
5) The ability to neutralize endotoxin-mediated cytokine production in whole blood ex vivo.
6) The ability to prevent septic shock in mice challenged with lethal doses of endotoxin.
7) The ability to prevent septic shock in mice challenged with lethal doses of live pathogenic bacteria.

APPLICATIONS OF THE INVENTION

As a consequence of the unique properties of the synthetic peptides applications could include:

1) Treatment of topical and systemic infections by multi-drug-resistant bacteria with peptide alone or in combination with conventional antibiotics.
2) Quantitative removal of endotoxins from physiological and pharmaceutical solutions.
3) Development of a new endotoxin assay, termed the Endotoxin Inhibition ELISA (EIE) on a commercial basis for clinical diagnostic use with the use of biotinylated peptide derivatives.
4) Prevention of sepsis by prophylactic use of peptides of the invention after surgery of high risk patients.
5) Treatment of the septic shock syndrome in mammals including humans.

Considering the general membrane destabilizing properties of amphipathic α-helical peptides as well as the demonstrated antitumor as well as the predicted antifungal, antiviral and anti-inflammatory properties, other possible applications of the synthetic peptides of the invention include:

6) Treatment of the infectious disease caused by the systemic merezoite forms of the malaria parasite Plasmodium spp.
7) Treatment of other parasitic diseases such as Trypanosomiosis.
8) Treatment of topical and systemic malignancy.
9) Treatment of fungal infections.
10) Treatment of viral infections.
11) Treatment of inflammation.

OBJECTIVES

Accordingly the primary object of the invention is to employ the novel peptides in the further development of a new endotoxin assay on a commercial basis for clinical diagnostic use.

It is also an object of the invention to provide novel prophylactic peptides for use in the prevention of septic shock.

It is also an object of this invention to provide novel therapeutic peptides for use in the treatment of septic shock.

It is also an object of the invention to provide novel peptides for the quantitative removal of endotoxins from pharmaceutical solutions.

It is also an object of the invention to provide novel therapeutic peptides for the treatment of infectious diseases in general.

Figure 1:
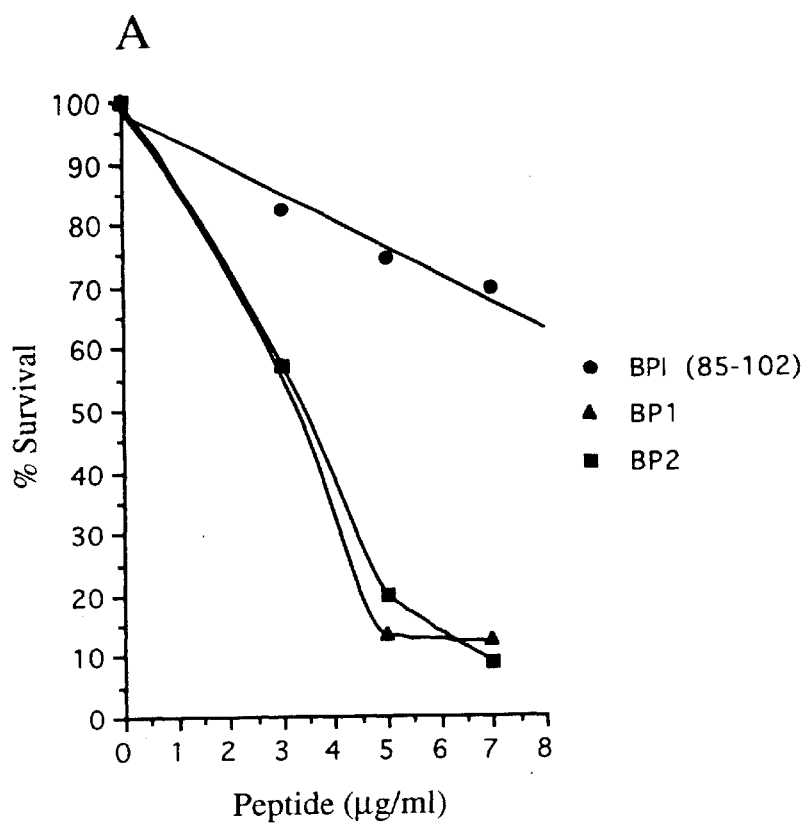
FIGS. 1A and 1B. The effect of synthetic peptides on the survival of *E. coli* 0111:B4 (panel A) or *S. aureus* (panel B). Logarithmically growing bacterial cells at a density of $10^7$ cells/ml in Luria-Bertani (LB) medium were incubated with synthetic peptides at concentrations of 3, 5 and 7 μg/ml (1, 2 and 3 μM) at 37° C. for 1 h and the residual cell density expressed as a percentage of the value obtained from bacterial cultures without added peptides.
Figure 1:
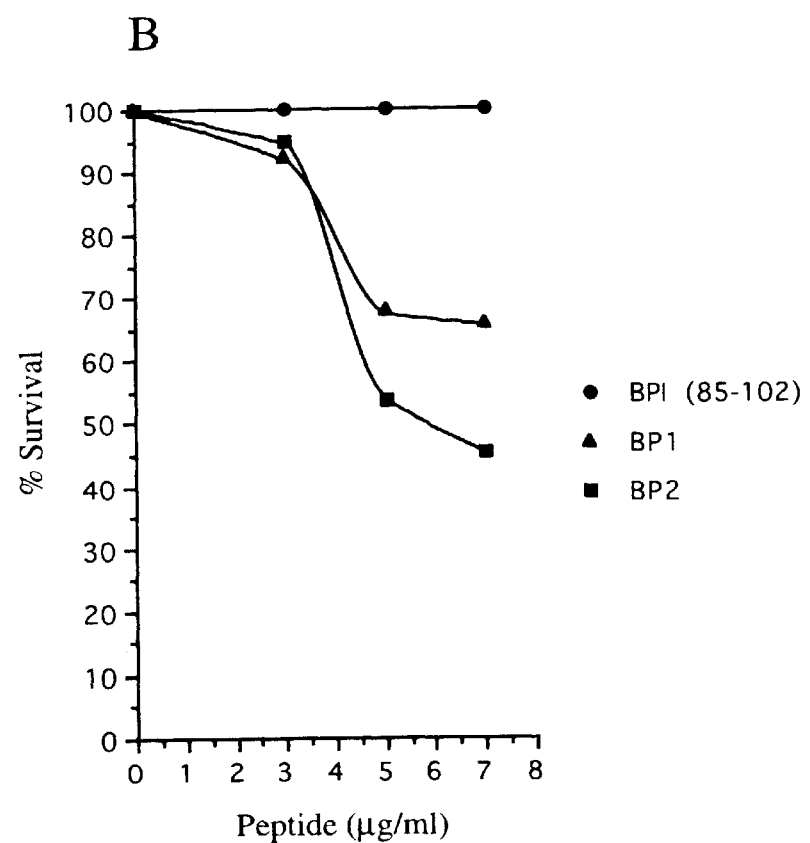

μg/Kg plus lethal concentrations of purified *E. coli* 0111:B4 LPS at 5 or 11 μg/Kg. Control groups only received Actinomycin D plus LPS. Survival was recorded at 24 h intervals during a 7 day period of observation. The indicated values are the combined results of three independent experiments.

FIG. 14. Efficacy of synthetic peptide BP2 on survival in a murine model of lethal peritonitis. Outbred female Swiss-Webster mice of 7 to 8 weeks, weighing 28 to 30 g were administered a predetermined lethal dose of 104 colony forming units (CFU) of the pathogenic strain of live *E. coli* 0118:K1:H7 Bort organisms by intraperitoneal (i.p.) administration in 0.5 ml pyrogen-free saline. After a delay of 1 h after infection, treated groups of mice received synthetic BP2 peptide in p.f saline at a dosage of 100 μg/mouse (approximately 4 mg/kg) and negative control groups only saline. Survival was recorded at 12 or 24 h intervals during a 7 day period of observation. The indicated values are the combined results of two independent experiments.

DETAILED DESCRIPTION OF THE INVENTION

Theoretical Considerations in the Design of the Novel Peptides

The paradigm used in the design process of the synthetic peptides involved 3 steps: i) identification of the amino acid side-chains (pharmacophoric groups) that may be responsible for Lipid A binding, ii) determination of the spatial arrangement of these groups, and iii) design of a peptide backbone upon which these groups are mounted in a way so as to retain a specific spatial orientation for optimal ligand binding.

On the basis of primary amino acid sequence and secondary structure comparisons together with molecular modelling of potential LPS-binding domains of naturally occurring anti-LPS and antibacterial proteins/peptides of mammalian, amphibian and insect origin, as well as functional comparisons relating to biological activity, a new generation of synthetic LPS-binding peptides of the invention was derived. Objectives included in the design were restricted size, optimized amphipathic α-helical structures with tandem arrays of potential LPS binding motifs, consisting of cationic and hydrophobic residues positioned in a specific orientation with respect to the helix for optimal binding to the negatively charged phosphate and hydrophobic groups of Lipid A. In addition, an approximately equal proportion of hydrophobic and basic amino acid residues was maintained in the composition of the peptides to ensure adequate solubility in aqueous solutions.

Structural Features of the Novel Peptides

The invention provides a formula for novel peptides with an amino acid composition such that the peptide is amphipathic, cationic, forms a stable α-helix and has the following amino acid sequence comprising at least 12 amino acids:

$R_1$-$R_2$-$A_1$-$B_1$-$(A_2$-$B_2$-$C_1$-$A_3)_m$-$(C_2)_n$-$R_3$, wherein A=an amino acid selected from the basic amino acids Lys,Arg or His
B=an amino acid selected from the aromatic amino acids Phe, Trp or Tyr
C=an amino acid selected from the group comprising the hydrophobic amino acids Leu, Ile, Val or Ala, and said peptide has either the orientation according to the formula or the retro orientation thereof, wherein at least 0-m of the repetitive sequence motifs ($A_2$-$B_2$-$C_1$-$A_3$) have the retro orientation and the remaining repetitive motifs ($A_2$-$B_2$-$C_1$-$A_3$) have the orientation as presented in the formula and wherein:

$R_1$-$R_2$- and $R_3$ are a number of amino acids, said number preferably ranging from 0–15 for the combination of $R_1$ and $R_2$ and for R3 separately and wherein
m=1–10, preferably 2–8, more preferably 2–5 and
n=1–3.

From the examples a value of n=3 is clearly a suitable embodiment. A further suitable peptide comprises $R_2$ selected from the group of sequences consisting of $A_4C_3A_5A_6$, wherein A and C are as defined above for A and C. Suitable other meanings of $R_1$ are $Gly_p$, wherein p=0–10 and $Ala_q$, wherein q=0–10. A peptide according to the invention must not be too long as this reduces the efficacy. Suitably $R_1R_2$- and $R_3$ will each comprise a number of amino acids ranging from 1–10. A peptide wherein either $R_1$-$R_2$- or $R_3$ or both are absent also is covered by the invention. A peptide wherein $R_1$-$R_2$- or $R_3$=a number of amino acids ranging from 1–5, preferably from 1–3 forms a suitable embodiment of the invention. As is apparent from the examples a peptide according to the invention wherein $R_1$-$R_2$- or $R_3$=1 amino acid functions remarkably better than the prior art peptides tested as well as better than other derivatives. The nature of the amino acids of $R_1$-$R_2$- or $R_3$ is less critical than the portions designated A B and C. The combination of the amino acids forming the peptide must in total however result in a cationic amphiphatic molecule. The composition of $R_1$-$R_2$- or $R_3$ can be such that it comprises an amino acid different to those of group A, B or C. The peptide can even only comprise $R_1$-$R_2$- or $R_3$ with amino acids different to those of A, B and C. The peptide can be linear or cyclic, monomeric or polymeric.

In general the peptide length according to the invention should not exceed 50 amino acids. Suitable size for a peptide according to the invention will be 12–40, preferably 12–30 amino acids in length. Any length comparable to the amino acid sequences illustrated in the examples is suitable. A length of 15–25 amino acids falls within this definition.

Although the total length of the peptide according to the invention, when used as a medicament, preferably does not exceed 50 amino acids, the total length may be longer when used in diagnosis. In particular the essential sequence as disclosed above can be contained in a longer peptide sequence; such longer peptide sequences may comprise spacers and the like, for allowing coupling to carriers or to other diagnostic aids, for example as fusion proteins.

Such fusion proteins and their production are well-known in the art and include, but are not limited to, glutathione-S-transferase, maltose binding protein, metal-binding polyhistidine, green fluorescent protein, luciferase and beta-galactosidase. The peptide may also be coupled to non-peptide carriers, tags or labels that facilitate tracing of the peptide, both in vivo and in vitro, and allow for the identification and quantification of binding of the peptide to substrates. Such labels, tags and carriers are well-known in the art and include, but are not limited to, biotin, radioactive labels and fluorescent labels.

The amino acids defined above may be L-amino acids or D-amino acids or mixtures thereof Further, it is to be understood that non-natural amino acids can be used instead of the corresponding natural amino defined above. Thus, in the definition of A, α,γ-diaminobutyric acid, α,δ-diaminovaleric acid (ornithine), α-amino-ε-amidinocaproic acid (indospicine), and the like are equivalents of lysine, arginine and histidine; in the definition of B, homo-phenylalanine, β-naphthyl-alanine, thyronine, and the like are equivalents of phenylalanine, tryptophan and tyrosine: and in the definition of C, α-aminobutyric acid, α-aminovaleric acid (norvaline), norleucine and the like, are equivalents of leucine, isoleucine, valine and alanine.

As stated above, the peptide may have the orientation of the formula given above or may have the retro orientation as a whole or in part. Any of the repetitive sequences can thus be in the retro orientation i.e. (A-C-B-A) or the orientation given in the formula, wherein the remaining groups are in the orientation as given in the formula. In a suitable embodiment as is apparent from the examples a peptide has the repetitive sequence (A-B-C-A) present in the retro orientation more often than in the orientation as presented in the formula, and/or at least one repetitive sequence has the orientation of the formula (ABCA) and at least one has the retro orientation (ACBA). It is to be noted that in repetitive sequences A, B and C may be different from each other, e.g. $A_2$ may be Lys in the first sequence and Arg in the second, etc. Examples of amphiphilic cationic peptides of the formula are:

BP 1 Gly-Arg-Leu-Arg-Lys-Lys-Trp-Lys-Ala-Phe-Lys-Lys-Phe-Leu-Lys-Ile-Leu-Ala-Cys (SEQ ID NO. 1)

BP2 Gly-Lys-Trp-Lys-Leu-Phe-Lys-Lys-Ala-Phe-Lys-Lys-Phe-Leu-Lys-Ile-Leu-Ala-Cys (SEQ ID NO. 2)

BP2.3 Gly-Lys-Tip-Lys-Ala-Phe-Lys-Lys-Ala-Phe-Lys-Lys-Phe-Ala-Lys-Ile-Leu-Ala-Gly (SEQ ID NO. 3)

BP2.4 Gly-Lys-Trp-Lys-Leu-Pho-Lys-Lys-Ala-Phe-Lys-Lys-Phe-Leu-Lys-Ile-Leu-Ala-Gly (SEQ ID NO. 4)

BP2.5 Cys-(Gly)$_9$-Lys-Trp-Lys-Ala-Phe-Lys-Lys-Ala-Phe-Lys-Lys-Phe-Ala-Lys-Ile-Leu-Ala-Cys-Gly (SEQ ID NO. 5)

Examples of cationic peptides similar to those of the formula according to the invention are:

BP1.1 Gly-Lys-Leu-Lys-Lys-Lys-Trp-Lys-Ala-Ala-Lys-Lys-Phe-Leu-Lys-Lys-Cys-Ser (SEQ ID NO. 6)

BP2.1 Gly-Lys-Trp-Lys-Leu-Phe-Lys-Lys-Ala-Ala-Lys-Lys-Phe-Leu-Lys-Lys-Cys-Ser (SEQ ID NO. 7)

BP2.2 Gly-Lys-Trp-Lys-Ala-Phe-Lys-Lys-Ala-Ala-Lys-Lys-Phe-Ala-Lys-Lys-Cys-Ser (SEQ ID NO. 8)

Where required, a biotin label was introduced at the C-terminal Cys after synthesis or in situ at the N-terminal during the last cycle of peptide synthesis. Peptides BP1 and BP2 were biotinylated at the thiol group of the C-terminal Cys with the use of Biotin-HPDP (Pierce Chemical Company, Rockford, Ill.) and BP2.1 and 2.2 with the use of a biotinylated N-terminal Gly residue.

The synthetic peptides are useful as novel antibiotics for the elimination of multi-drug resistant (MDR) bacteria, for the detection of femtomolar amounts of endotoxin, for the detoxification of endotoxins in biological fluids or pharmaceutical preparations and in the prevention or treatment of septic shock in mammals including humans. The recommended dosage for use in the prophylaxis or treatment of septic shock initiated by bacterial infection is estimated to be in the range of 0.1 to 0.5 mg/kg body weight depending on the risk of infection or severity of the disease condition. The compounds may be administered parenterally using well known pharmaceutical carriers or inert diluents. The compounds can be stored in dry form and dissolved in diluent, preferably pyrogen-free saline immediately prior to administration. The novel peptides may be synthesized by classical methods of peptide chemistry using automated or manual techniques well known in the art. Such technology is considered to be incorporated by reference. An example is Merrifield Sythesis or PEPSCAN. The examples of the description provide illustration of a synthesis process that can suitably be applied.

Description of the Preferred Embodiments

The procedure used in the synthesis of the peptides of the invention employed conventional Fmoc (9-fluorenylmethoxycarbonyl) solid-phase chemistry. In the automated procedure, A MILLIGEN Model 9050 peptide synthesizer (MILLIPORE, Burlington, Mass.) was loaded with 0.05 mmole of N-α-Fmoc-L-amino acid substituted NovaSyn TGA resin (Calbiochem-Novabiochem AG, La üfelfingen, Switzerland). N-α-Fmoc-L-amino acid-O-pentafluorophenyl residues (Fmoc-aa) of the required amino acids were used in the sequential synthesis of the peptide. Side chain protecting groups of the N-α-Fmoc-protected amino acid were as follows: t-butyloxycarbonyl (Lys, Trp), 2,2,5,7,8-pentamethylchroman-6-sulphonyl (Arg) and t-butyl (Cys, Ser). The immobilized C-terminal Fmoc-protected amino acid, was treated with piperidine (20% v/v) to remove Fmoc from the α-amino group. Four equivalents of each N-protected amino acid were activated and coupled with a five-fold molar excess of TBTU/HOBt (2-(1H-benzotriazole-1-yl)-1,1,3,3-tetramethyluronium tetrafluoroborate/N-hydroxybenzotriazole). After completion of the synthesis, the peptide was simultaneously cleaved from the resin and deprotected using 92% (v/v) TFA in the presence of 2% (w/v), phenol 2% (v/v) water and 2% (v/v) ethanedithiol and 2% (v/v) thioanisole as scavengers. Free peptides were separated from the resin by filtration, repeatedly extracted with ethyl ether and purified by reverse-phase high pressure liquid chromatography (RP-HPLC) on a $C_{18}$ column (Delta-Pak, Waters, Bedford, Mass.) using a 0–60% acetonitrile gradient in 0.05% TFA. The purity of the synthetic peptides was determined by analytical RP-HPLC and amino acid analysis by the Pico-Tag method (Waters, Bedford, Mass.). Purified peptides were stored at −70° C. either in lyophilized form or in pyrogen-free water at a concentration of 2 mg/ml.

Experimental Observations

Antibacterial Activity

Bactericidal activity of the peptides of the invention was demonstrated by determining the effect on survival of representative Gram-negative (*Escherichia coli* serotype 0111:B4) and Gram-positive (*Staphylococcus aureus*) bacteria in liquid culture relative to a control without added peptide. A peptide encompassing a selected LPS-binding domain from a well characterized human antiendotoxin protein, known as bactericidal/permeability increasing protein (BPI), from amino acids 85 to 102, denoted as $BPI_{(85-102)}$, was included for a direct comparison of the efficacy of the endotoxin-binding domain of a naturally occurring protein and the synthetic peptides of the invention. The amino acid sequence of the $BPI_{(85-102)}$ peptide is:

Ile-Lys-Ile-Ser-Gly-Lys-Trp-Lys-Ala-Gin-Lys-Arg-Phe-Leu-Lys-Met-Ser-Gly-(Cys) (SEQ ID NO. 9)

The $BPI_{(85-102)}$ reference peptide was synthesized as previously described for peptides of the invention and provided with a C-terminal Cys residue for the purpose of biotinylation as previously described. A dose-dependent reduction in the cell-density of both Gram-negative and Gram-positive bacterial cultures was evident with BP1 and BP2, contrary to the $BPI_{(85-102)}$ peptide, which showed a slight effect on Gram-negative bacteria and no effect on Gram-positive bacteria (Table 1). Incubation of various concentrations of the synthetic peptides according to the invention for a limited time period on the survival of both types of bacteria again illustrated their potent anti-microbial activity as opposed to that of the $BPI_{(85-102)}$ peptide (FIG. 1) with the sequence corresponding to that of the potential LPS binding domain of the native BPI protein. This is indicative of a broad specificity of the synthetic peptides, in keeping with the general bactericidal properties of this class of linear amphipathic α-helical peptides. To demonstrate the influence of peptide sequence as defined by the formula of the invention on antibacterial properties, analogues were designed so as to contain subtle sequence differences compared with the representative BP1 and BP2 peptides of the invention. The absolute requirement for a tandem array of 2 or more of the repetitive sequence motifs $(A_2-B_2-C_1-A_3)_m$, flanked by a hydrophobic C-terminal domain $(C_2)_n$, was demonstrated with the use of the BP1.1, BP2.1 derivatives. The $B_2$ residue in the N-terminal repetitive sequence element in each instance, instead of an aromatic amino acid residue, as specified by the formula of the invention, was replaced with an Ala residue and the hydrophobic $(C_2)_n$ element made hydrophilic by substitution with Lys and Cys residues. Although the overall homology between these derivatives and that of the parent peptides according to the invention is high, no detectable anti-microbial activity of the derivatives was apparent even at the highest concentration tested (20 µg/ml). The BP2.3, BP2.4 and BP2.5 peptides according to the invention displayed similar anti-microbial efficacy as the BP2 peptide under the same conditions (data not shown).

An additional series of experiments were performed to investigate the antibiotic properties of peptides of the invention under simulated physiological conditions in whole blood ex vivo, against a clinically relevant pathogenic Gram-negative bacterium (*Escherichia coli* 018:K1:H7 Bort). In a typical example, BP2 peptide at a concentration of 5 µg/ml (2 µM) effected a 95% reduction of viable bacteria from an initial concentration of $10^6$ colony forming units (CFU)/ml of citrated whole blood, within 20 minutes of incubation at 37° C. to a >99% reduction after 1 h compared to samples without added peptide (data not shown). These results illustrate potent antimicrobial properties of the peptides of the invention against microbial pathogens in whole blood and suggest a high therapeutic potential for the treatment of clinical bacteremia.

LPS-binding Properties

Figure 2:
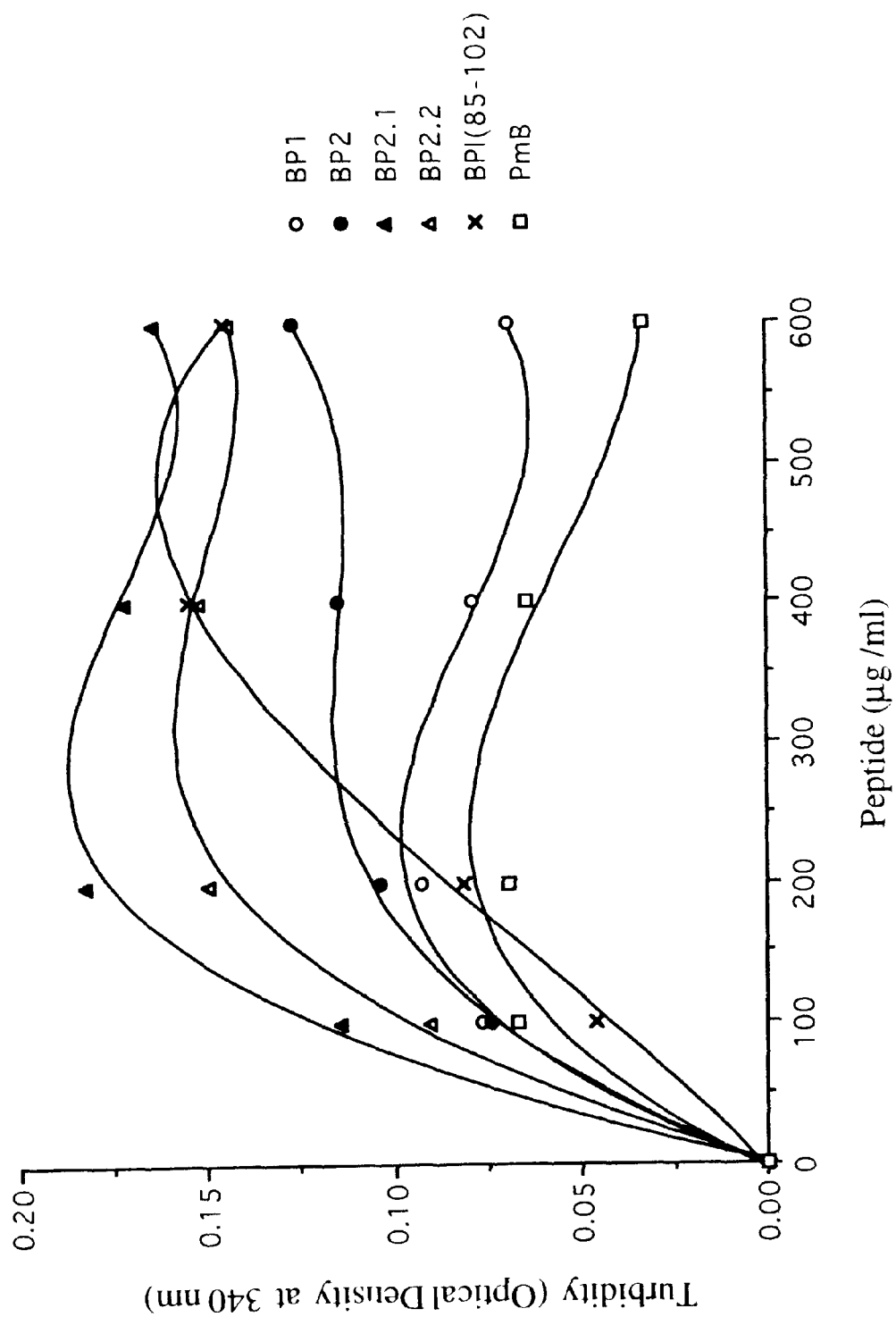
FIG. 2. Endotoxin complexation activity of the synthetic peptides. Peptides at concentrations of 100 to 600 μg/ml were incubated with *E. coli* D31m4 Re or J5 LPS at 100 μg/ml in a total volume of 100 μl pyrogen-free phosphate buffered saline (PBS) in plastic ELISA microtiter plates for 30 min at 23° C. The turbidity produced by the insoluble peptide-endotoxin complexes was measured at 340 nm. The values represent the mean of three determinations and were corrected for controls containing the same concentrations of endotoxin or peptide.
Figure 3:
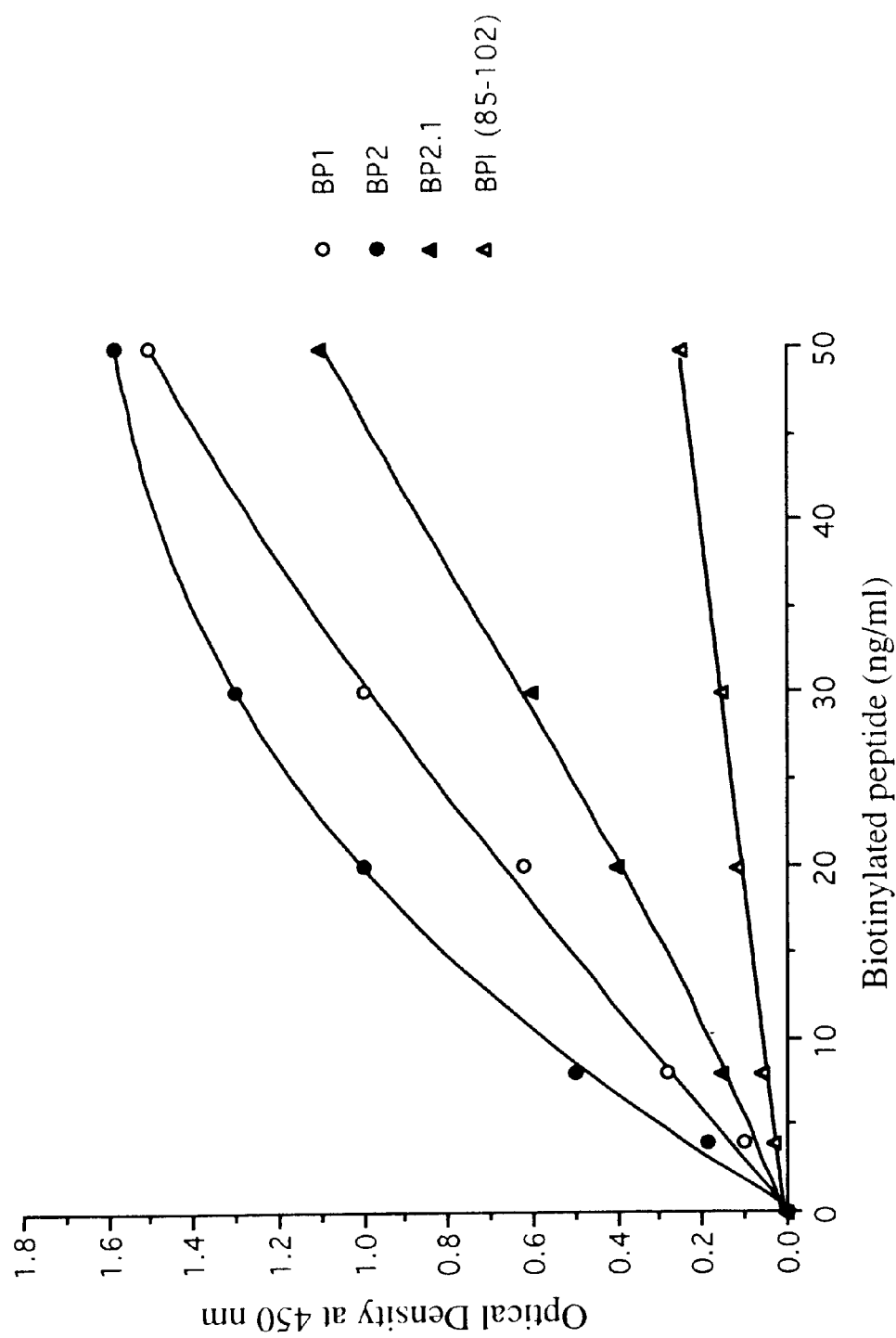
FIG. 3. Lipid A binding affinity of the synthetic peptides. Plastic ELISA microtiter plates were coated with purified *E. coli* D31m4 Lipid A at 1 μg/ml. Incubations were for 20 min with the indicated concentrations of synthetic peptides BP1, BP2 or BP2.1 or control peptide $BPI_{(85-102)}$ followed by streptavidin-HRP at a dilution of 1 in 20 000. Washing steps to remove excess peptide or streptavidin were with 50 mM Tris buffer pH 7.4 containing 0.05% (v/v) Tween 20. Development was with TMB substrate for 10 min. The optical density (O.D) at 450 nm was measured with a microplate reader and values were corrected for non-specific binding which was generally between 5 and 10%. The plotted values are the corrected means of triplicate experiments.
Figure 4:
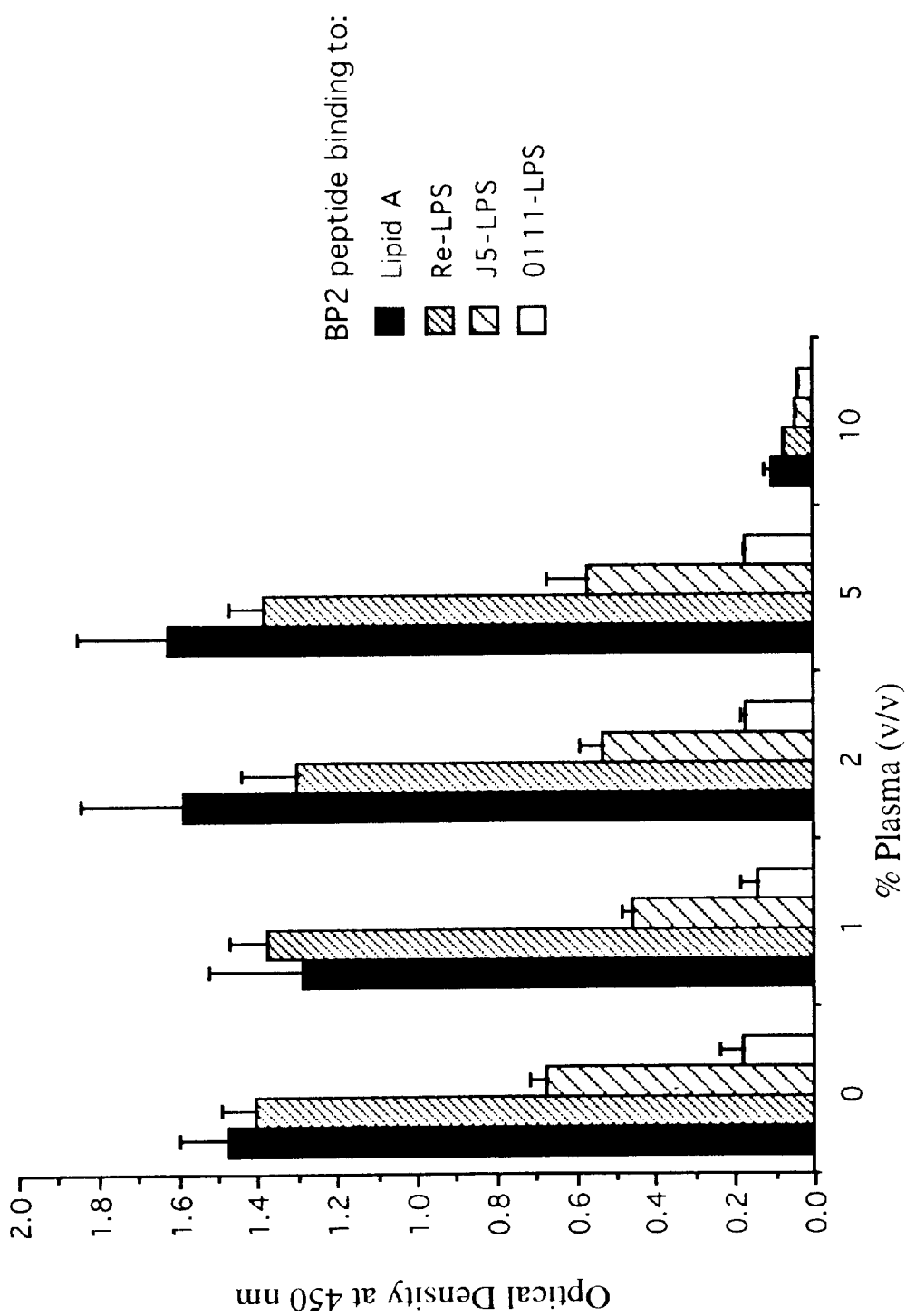
FIG. 4. Effect of endotoxin complexity and plasma concentration on the binding of synthetic peptide BP2 of the invention to immobilized LPS. Coated ELISA microtiter plates containing *E.coli* D31m4 Lipid A, Re, J5 or 0111:B4 LPS were incubated with synthetic peptide at a concentration of 40 ng/ml in the presence of plasma at dilutions to 10% (v/v). Binding activity was determined by the ELISA microplate lipid A binding assay as previously described.

Specific binding of the synthetic peptides of the invention to isolated heterologous LPS via the Lipid A moiety was demonstrated by double-immunodiffusion, turbidity and ELISA microplate endotoxin binding techniques. Double-immunodiffusion of the peptides of the invention against 'rough' R-type *E. coli* D31m4 Re-LPS (List Biological Laboratories Inc., Calif.) or the structurally more complex 'smooth' S-type *E. coli* 0111:B4 LPS (Sigma Chemical Co., Rockford, Ill.) was performed in 0.8% (w/v) agarose containing 50 mM Tris and 0.1% (w/v) Triton X100, pH 7.5. for 16 h at 20° C. PmB and $BPI_{(85-102)}$ were included as control compounds for comparative purposes. The microprecipitates formed were visualized by Coommassie brilliant blue staining. The results clearly demonstrated a concentration dependent precipitation of Re and 0111 LPS by the peptides according to the invention (data not shown). The amount of precipitate generated by the peptides with Re LPS at the same molar ratio of peptide to LPS, was comparable to that with PmB, indicating a similar affinity of the synthetic peptides for Lipid A. PmB, however, failed to precipitate 0111 LPS in this system. The fact that the $BPI_{(85-102)}$ peptide precipitated considerably less Re or 0111 LPS demonstrated a markedly higher affinity of peptides according to the invention for endotoxin than $BPI_{(85-102)}$. Since the amount of precipitate formed is a function of valency, the peptides of the invention appear to be capable of a high degree of intermolecular binding of LPS molecules via the Lipid A moieties. Measurement of the amount of endotoxin complexation by comparison of the staining intensity of insoluble precipitates with varying peptide to endotoxin molar ratios, indicated that the stochiometry for optimal complexation of endotoxin by the synthetic peptides according to the invention is 1 mole of peptide to 2 moles of endotoxin. A turbidity assay was employed for a direct comparison of the endotoxin-binding activity or avidity of selected synthetic peptides according to the invention using the 'rough' serotypes *E. coli* Re or Rc (J5) LPS. PmB and $BPI_{(85-102)}$ were included as control compounds for comparative purposes. The degree of precipitation of endotoxin by the synthetic peptides according to the invention was determined by measurement of the optical density of insoluble complexes formed at 340 nm (FIG. 2). In most instances optimal complexation of Re or J5 LPS by the synthetic peptides of the invention was evident at a molar ratio of peptide to endotoxin of 1 to 2. The control $BPI_{(85-102)}$ peptide was required at a 4-fold molar excess for approximately the same degree of complexation. The avidity, expressed as the degree of insoluble peptide-endotoxin complex formation with a 2-fold molar excess of synthetic peptide under the conditions of the assay was BP2.1>BP2.2>BP2>BP1>PmB >$BPI_{(85-102)}$. There was no significant difference between complexation of Re or the structurally more complex J5-LPS by the synthetic peptides. Determinations of the time-course of the precipitation reaction indicated that maximum precipitation of LPS occurs within 5 minutes at room temperature (data not shown). The Lipid A binding affinity of the synthetic peptides were directly compared in a solid-state endotoxin-binding assay. Binding characteristics of biotinylated derivatives of the synthetic peptides BP1, BP2, BP2.1 and the control peptide $BPI_{(85-102)}$ were determined on ELISA microtiter plates coated with *E. coli* D31m4 Lipid A. Specific binding of the biotinylated peptides to the immobilized Lipid A was determined by development with Streptavidin-HRP and 3, 5, 3', 5' tetra-methylbenzidine (TMB) substrate and expressed as the corrected optical density at 450 nm. The apparent binding affinities of the various peptides calculated by means of a Scatchard plot were: BP2 ($K_a=1.9\times10^8$ $M^{-1}$), BP1 ($K_a=0.9\times10^8$ $M^{-1}$), BP2.1 ($K_a=0.4\times10^8$ $M^{-1}$) and BPI $_{(85-102)}$ ($K_a=0.2\times10^8$ $N^{-1}$). Comparison of these binding affinities shows marked differences in affinity for Lipid A in the order BP2>BP1>BP2.1>$BPI_{(85-102)}$ (FIG. 3). In addition, the BP2 peptide exhibits an approximately 20-fold higher affinity for Lipid A compared with the known high affinity LPS binding molecule, Polymyxin B ($K_a=10^7$ $M^{-1}$). In this instance, the BP2 peptide displayed the highest degree of binding to the immobilized Lipid A, as opposed to the turbidity assay with LPS in solution, which indicates a greater potential for intramolecular binding than the other peptides. The affinity of the novel synthetic peptide BP2 for endotoxin of increasing complexity as well as the effect of plasma on binding was examined with the use of the ELISA microplate assay. The results (FIG. 4) show that the degree of binding of BP2 decreases with increasing complexity of immobilized LPS and may reflect steric hindrance by the long polysaccharide core and O-antigen side-chains of the more complex endotoxins under conditions of immobilization. The presence of up to 5% (v/v) heat-treated, clarified plasma had no significant effect on binding of the novel peptide BP2 to endotoxins of increasing complexity, indicating that the binding is specific and of high affinity.

Figure 5:
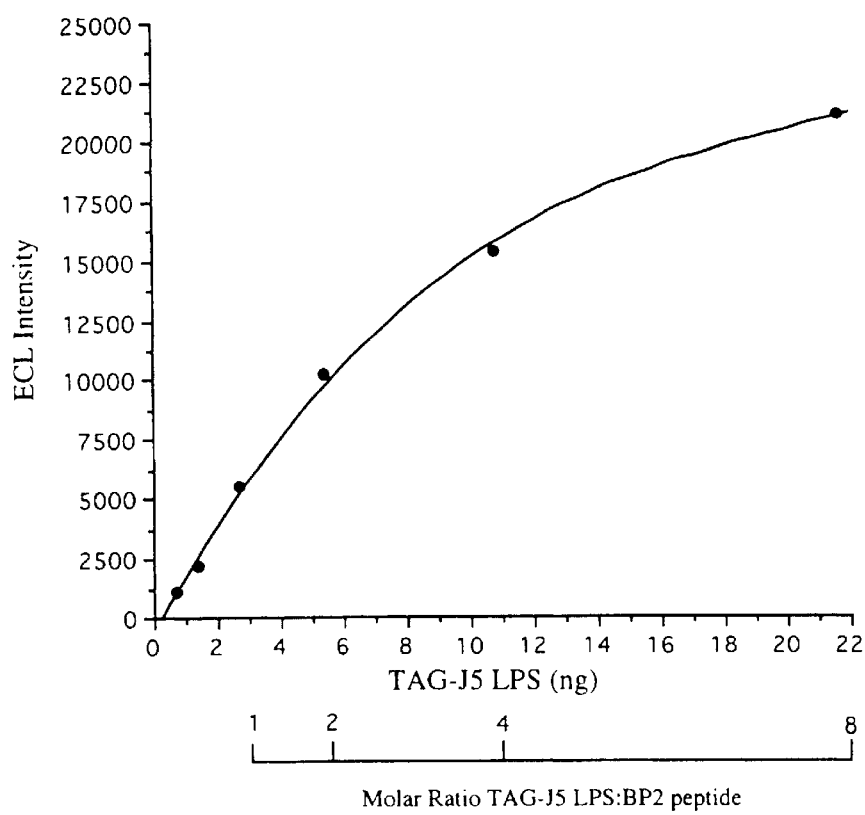
FIGS. 5A and 5B. Capture of labeled endotoxin by immobilized synthetic peptide. 2 ng of biotinylated synthetic peptide BP2, immobilized on 20 μg of streptavidin-coated supramagnetic polystyrene beads (Dynabeads M-280, Dynal A. S., Oslo, Norway) was incubated with the indicated amounts of chemiluminescent TAG-labeled *E. coli* J5 LPS for 20 min at 23° C. The amount of captured endotoxin, after a washing cycle with Phosphate buffer containing 0.1% (v/v) Triton X100, was determined by electochemiluminescence detection (ECL) using an Origen Analyser (Igen Inc., Rockville, Mass.). Panel A shows saturation of the lipid A binding activity of the synthetic peptide at an 8-fold molar excess of LPS. Panel B demonstrates a linear binding response up to a 2-fold molar excess of LPS. The values are the means of triplicate determinations corrected for non-specific binding.
Figure 5:
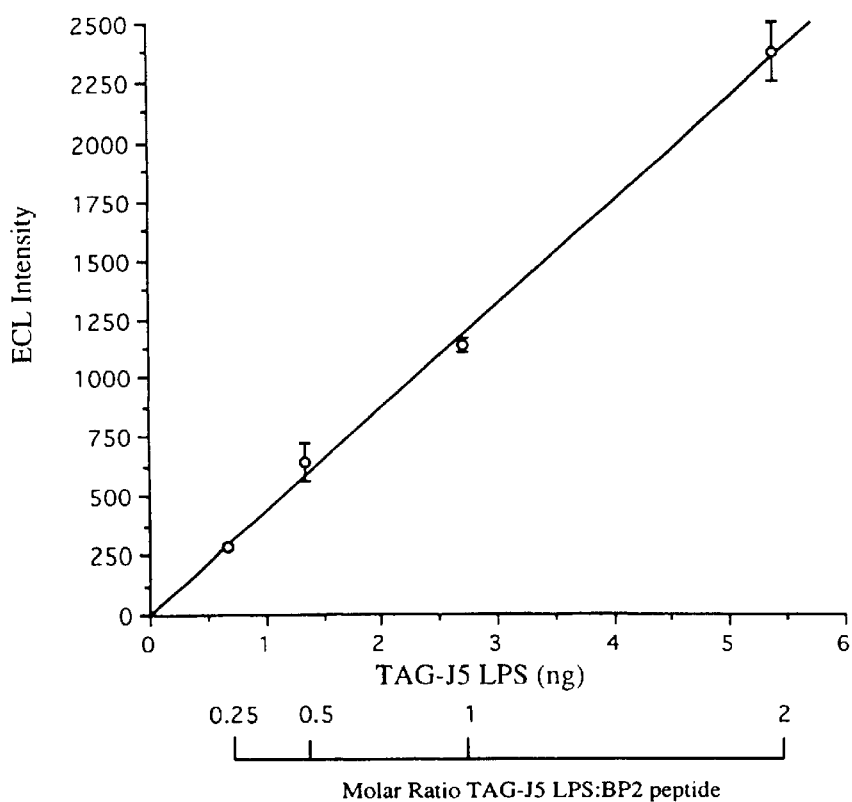
Figure 6:
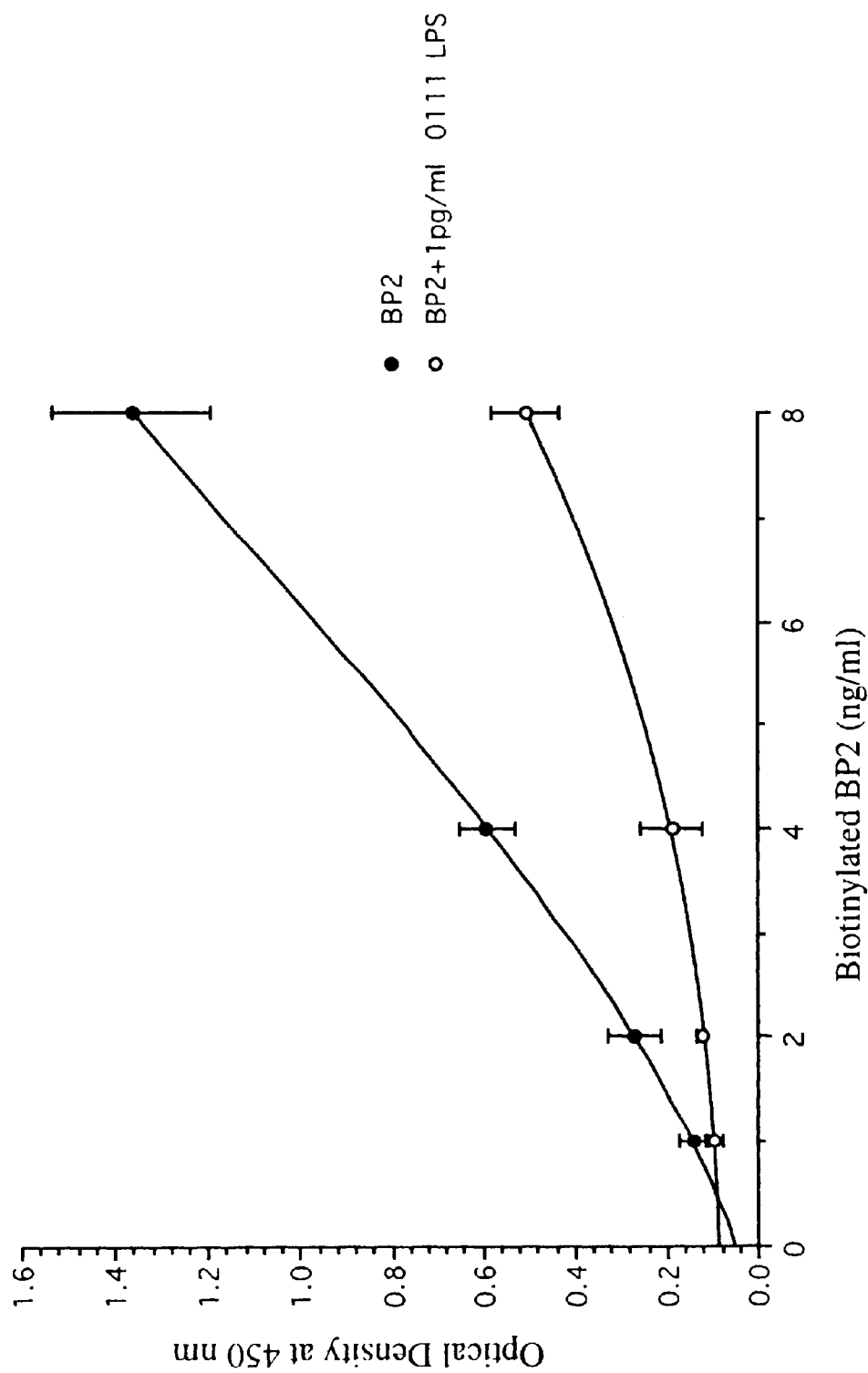
FIG. 6. Competitive inhibition of binding of synthetic peptide BP2 to immobilized lipid A by endotoxin. Biotinylated BP2 peptide in the indicated concentration range was pre-incubated with *E. coli* 0111:B4 LPS at 1 pg/ml for 20 min at 23° C. and the residual endotoxin binding activity was determined with the use of a lipid A binding ELISA microplate assay. Individual values are the means of triplicate experiments corrected for non-specific binding.
Figure 7:
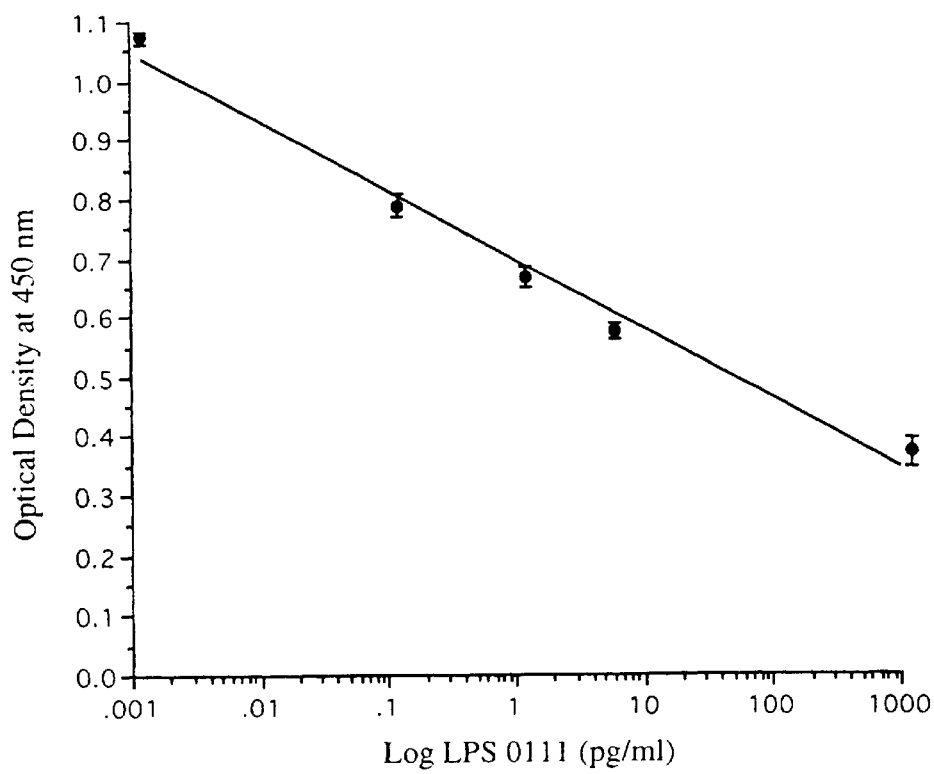
FIGS. 7A and 7B. Detection of endotoxin in solution with a Lipid A binding assay, the endotoxin inhibition ELISA (EIE) microplate assay. Dose-response of residual LPS binding activity of synthetic peptide BP2 at 8 ng/ml after pre-incubation with *E. coli* 0111:B4 LPS in the ranges from 0.1 to 1000 pg/ml (Panel A) or from 0.1 to 100 pg/ml (Panel B).
Figure 7:
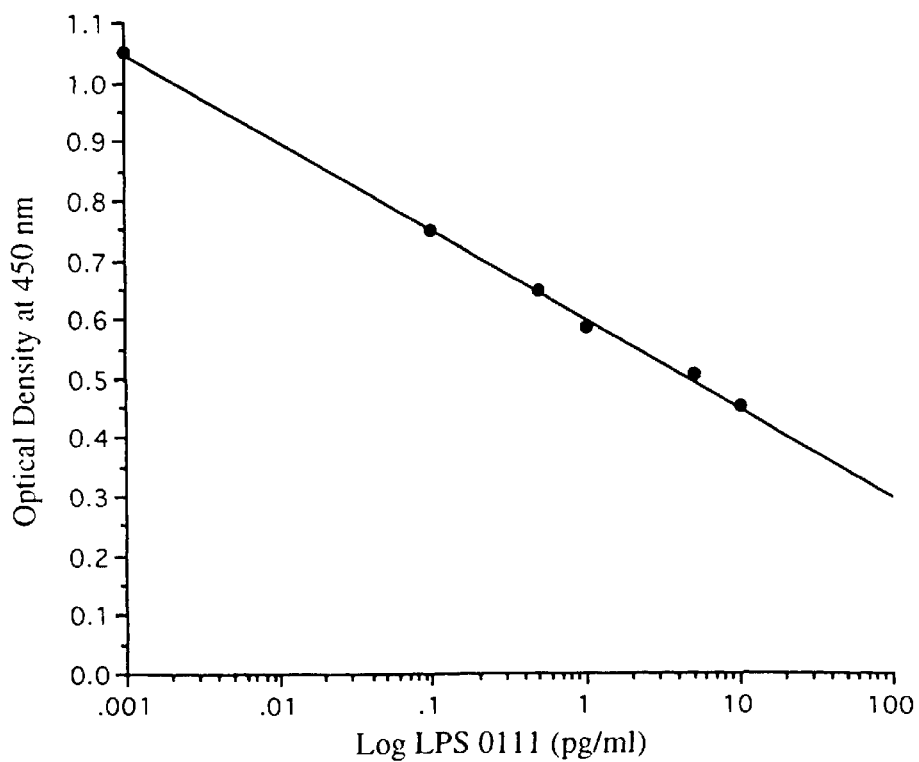

To determine the binding capacity of immobilized synthetic peptide BP2, which displayed the highest apparent binding affinity for Lipid A ($K_a=1.9\times10^8$ M$^{-1}$), streptavidin-coated supramagnetic polystyrene beads (Dynabeads M-280, Dynal A. S., Oslo, Norway), saturated with biotinylated BP2 peptide were incubated with various concentrations of E. coli J5 LPS, labeled with the use of a N-hydroxysuccinamide ester of a ruthenium (II) tris-bipyridine chelate (TAG-NHS-ester). Capture of the TAG labeled J5 LPS by immobilized synthetic peptide was quantitated by electrochemiluminescence detection subsequent to washing steps with phosphate buffer containing 0.1% (w/v) Triton X100 to remove excess unbound LPS. The results show a linear concentration-dependent capture of TAG-LPS by the immobilized peptide up to a stochiometric ratio of peptide to LPS of 1 to 2, reaching saturation with an 8-fold molar excess of endotoxin (FIG. 5). This confirms the high capacity of immobilized peptides of the invention for endotoxin in solution. These experiments demonstrate that the peptides of the invention bind to heterologous. LPS with high affinity and are universal lipid A binding ligands. The above mentioned microplate experiments were employed to determine the endotoxin binding activity and specificity of the synthetic peptides and formed the basis for the development of a novel highly sensitive endotoxin assay. Experiments utilizing the biotinylated BP2 peptide in an ELISA microplate Lipid A binding assay indicated that 1 pg/ml E. coli 0111:B4 LPS was capable of inhibiting binding of the synthetic peptide to immobilized Lipid A by 65% (FIG. 6). This competitive binding inhibition was found to be linear with 0111:B4 LPS concentrations from <0.1 to 1000 pg/ml in the presence of 1 to 5% (v/v) heat-treated, clarified EDTA plasma, with the lower limit of detection of this novel endotoxin assay at the femtomolar level (FIG. 7). The same degree of concentration-dependent inhibition was observed when various amounts of added endotoxin were assayed directly in plasma dilutions. The results demonstrate the preparation of a highly selective and sensitive agent to detect trace amounts of LPS in physiological fluids and pharmaceutical preparations by means of the Endotoxin Inhibition ELISA (EIE) microplate technique.

LPS-neutralizing Properties
In vitro Detoxification

Figure 8:
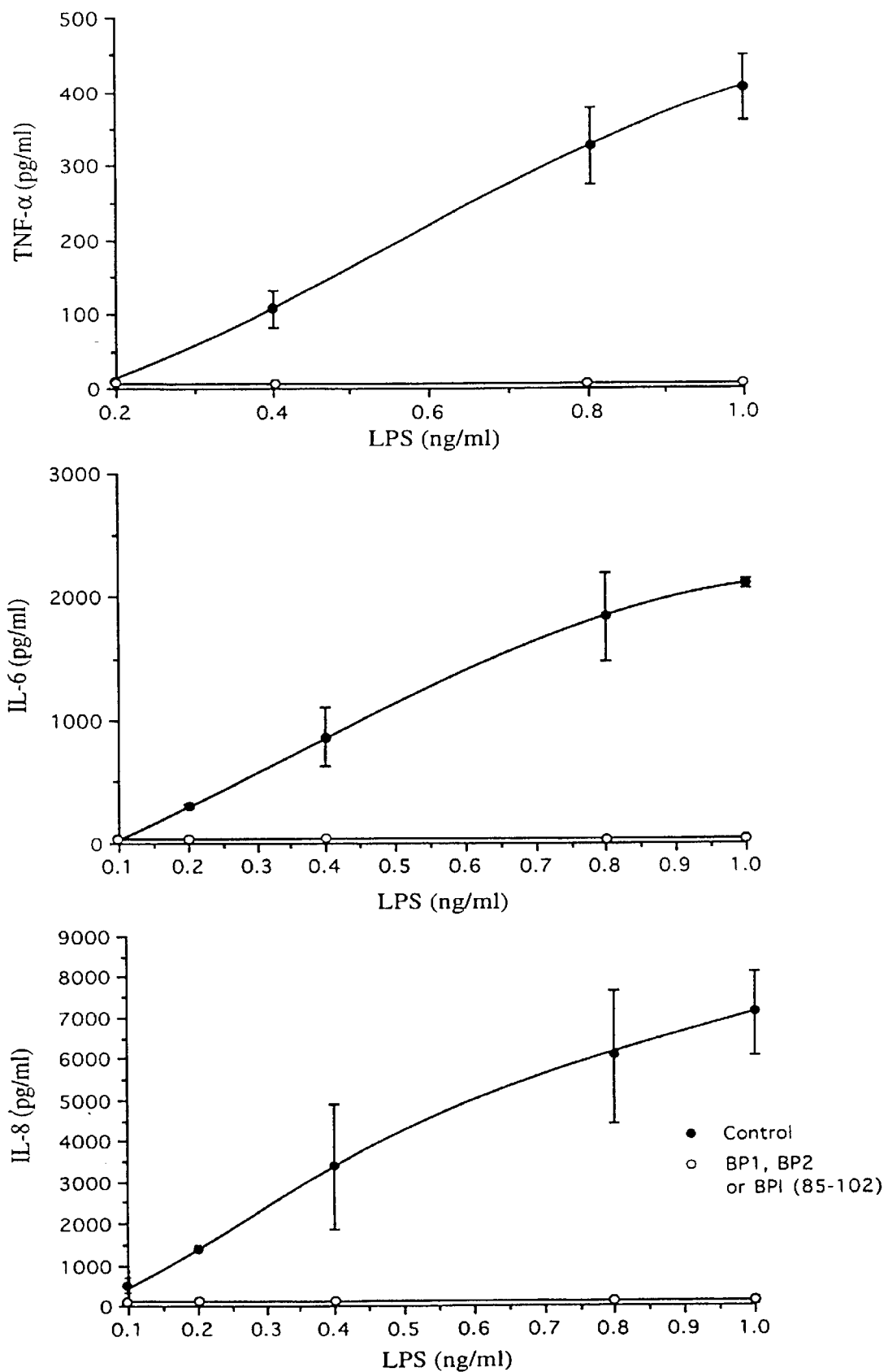
FIG. 8. Effect of pre-incubation of *E. coli* 0111:B4 LPS with synthetic peptides BP1, BP2 and control peptide $BPI_{(85-102)}$ on cytokine production in 1 in 10 diluted whole blood. The indicated amounts of *E. coli* 0111:B4 LPS from 0.1 to 1 ng/ml were pre-incubated with the synthetic peptides BP1 or BP2 or the control peptide $BPI_{(85-102)}$ at concentrations of 10 μg/ml for 30 min at 37 C. and the cytokine inducing ability of the LPS measured in diluted whole blood containing heparin at 100 I.U/ml after incubation for 16 h at 37° C. Each value is the mean of triplicate experiments. The controls contained only LPS.
Figure 9:
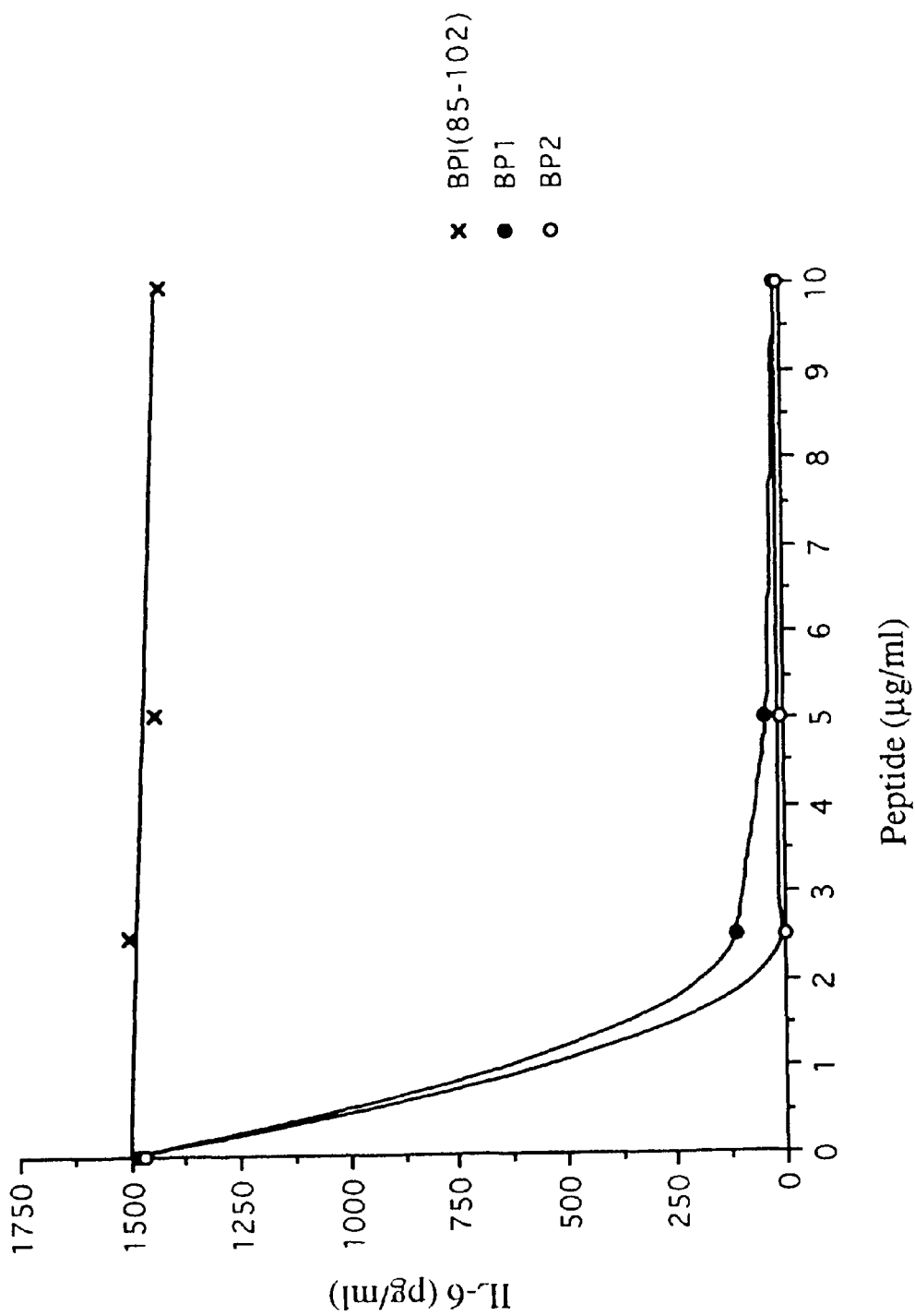
FIG. 9. Effect of simultaneous addition of *E. coli* 0111:B4 LPS and synthetic peptides on IL-6 production in whole blood diluted 1 in 10. Synthetic peptides BP1 or BP2 or the control peptide $BPI_{(85-102)}$ at the concentrations indicated, were added together with *E. coli* 0111:B4 LPS at 1 ng/ml to diluted whole blood containing heparin at 100 I.U/ml. IL-6 concentration was determined after incubation for 16 h at 37° C. Each value is the mean of triplicate experiments. Controls contained no added peptide.
Figure 10:
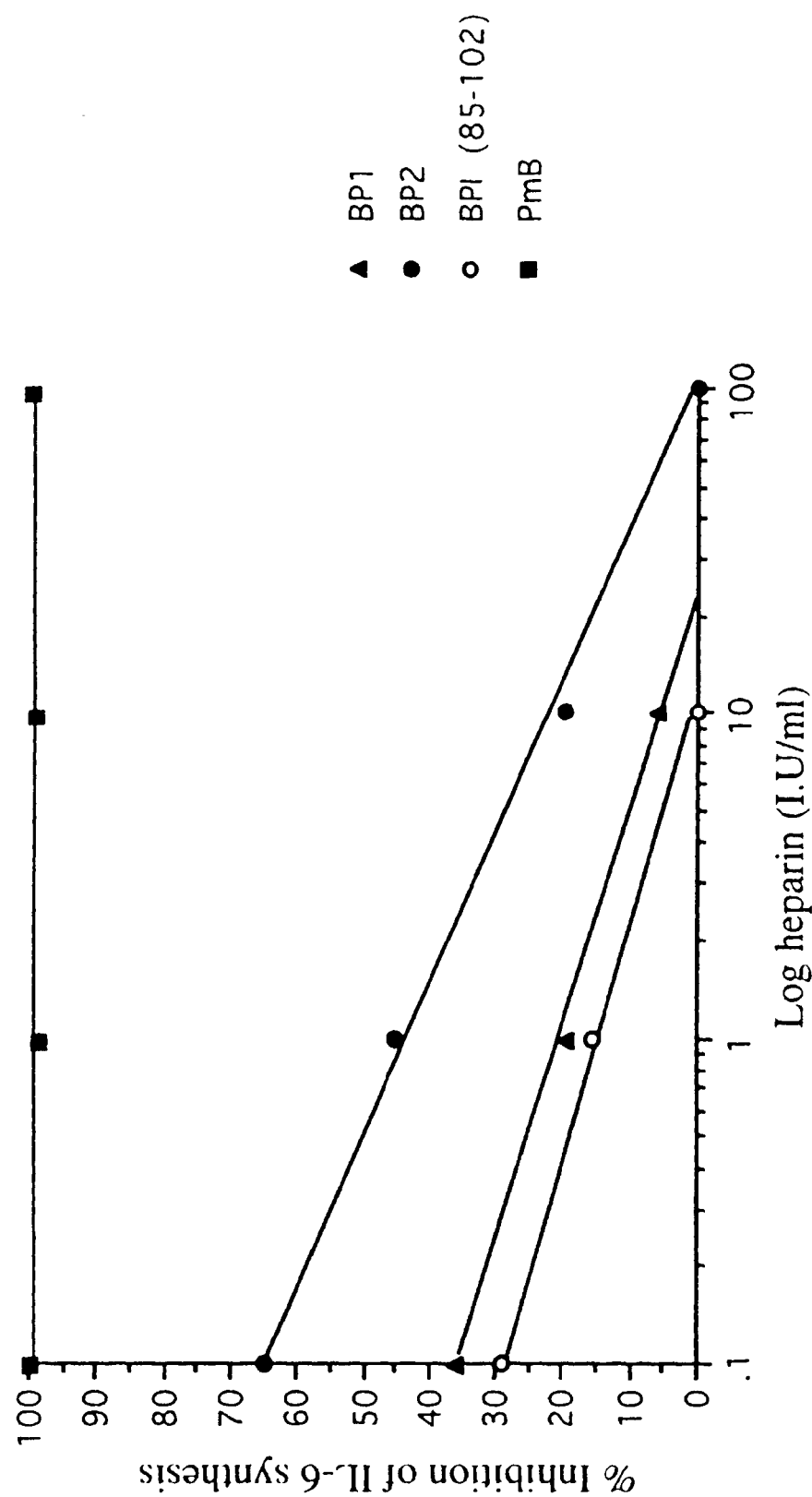
FIG. 10. Effect of heparin on the efficacy of neutralization of the IL-6 inducing ability of *E. coli* 0111:B4 LPS by synthetic peptide or Polymyxin B in whole blood diluted 1 in 10. Synthetic peptides at concentrations of 2 μg/ml or PmB at 1 μg/ml was pre-incubated for 30 min at 37° C. with *E. coli* 0111:B4 LPS at 1 ng/ml in RPMI medium containing heparin in the concentration range of 0.1 to 100 I.U/ml. The residual cytokine inducing ability of the treated endotoxin was determined in diluted whole blood containing heparin at 2 IU/ml after incubation for 16 h at 37° C. Each value is the mean of triplicate determinations corrected for background. Controls contained only LPS.

The endotoxin neutralizing activities of the synthetic peptides of the invention were evaluated by investigating the effect on LPS-stimulated release of the pro-inflammatory cytokines, tumor necrosis factor alpha (TNF-α), interleukin-6 (IL-6) or interleukin-8 (IL-8) in a well characterized in vitro human whole blood bioassay system. In one series of experiments, dilutions of E. coli 0111:B4 LPS from 0.2 to 1 ng/ml were pre-incubated with synthetic peptides at 10 µg/ml concentrations in RPMI medium for 30 min at 20° C. and added to diluted whole blood. Cytokine concentrations in the supernatants were determined after further incubation for 16 h at 37° C. in the presence of 5% $CO_2$ by specific and sensitive ELISA kits (CLB, Amsterdam, The Netherlands). In another series of experiments, the effects of synthetic peptides at concentrations of 2,5, 5 and 10 µg/ml on IL-6 induction by 1 ng/ml 0111:B4 LPS was examined after simultaneous addition of synthetic peptide and LPS to diluted whole blood. The results demonstrate total inhibition of the pro-inflammatory cytokines TNF-α, IL-6 or IL-8 production due to highly efficient neutralization of LPS by pre-incubation with the synthetic peptides of the invention (FIG. 8). Simultaneous addition of synthetic peptides and LPS showed that BPI or BP2 at concentrations as low as 1 µM were capable of completely inhibiting IL-6 production by endotoxin in the complex environment of whole blood (FIG. 9). The control peptide $BPI_{(85-102)}$ was ineffective in reducing cytokine production under these conditions even at a 4-fold higher concentration. This probably reflects the differences in binding affinity for Lipid A of BP1 and BP2 compared with the $BPI_{(85-102)}$ peptide of approximately 5 and 10-fold, respectively. An additional factor which may have influenced binding of the control peptide to endotoxin is the presence of heparin employed as an anti-coagulant at a concentration of 100 I.U/ml in the assay system. The consensus binding domain derived from a large number of heparin-binding proteins was found to partially overlap the potential LPS binding domains of the synthetic peptides indicating that the presence of heparin at a high enough concentration, could effectively compete with endotoxin for binding to the synthetic peptides and effectively reduce the endotoxin neutralizing activity. On this basis, it was predicted that the extent of reduction of endotoxin neutralizing efficacy would be a function of the differences in affinity between peptides for endotoxin and heparin. To verify this hypothesis, a series of experiments to determine the effect of increasing heparin concentrations on the efficacy of endotoxin neutralization during pre-incubation of synthetic peptide and E. coli 0111:B4 LPS were performed. FIG. 10 illustrates a dose-dependent suppression of endotoxin neutralizing activity of the synthetic peptides by heparin as exemplified by a reduction of IL-6 inhibition. The LPS-neutralizing activity of PmB, included as a control, was not influenced over the heparin concentration range employed. Calculations with the use of the specific heparin concentration that would reduce the efficacy of binding of BP2 to LPS by 50% ($IC_{50}=0.4$ U/ml) indicates that an approximately 10,000-fold molar excess of heparin with respect to LPS is required for this degree of competitive inhibition of the BP2 peptide. This observation implies that the affinity of the synthetic peptide BP2 is considerably higher for LPS than for heparin. The LPS neutralizing efficacy of the synthetic peptides BPI and the control peptide $BPI_{(85-102)}$ were reduced by 75% and 80% respectively by the same heparin concentration indicating a relatively higher affinity of these peptides for heparin than for endotoxin.

Figure 11:
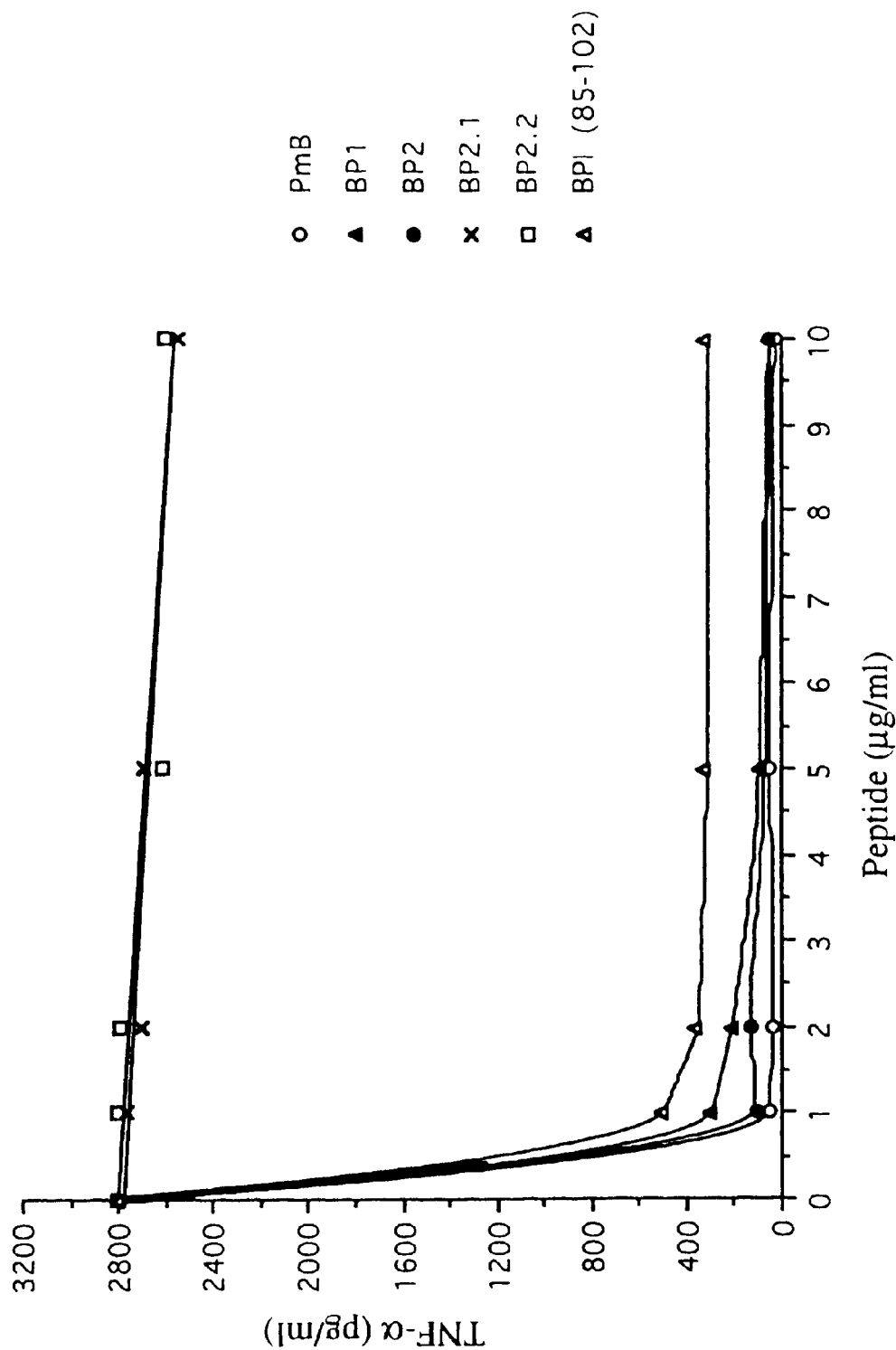
FIG. 11. Effect of pre-incubation of *E. coli* 0111:B4 LPS with synthetic peptides or Polymyxin B on TNF-α levels in whole blood ex vivo. The indicated amounts of synthetic, control peptides or PmB were pre-incubated with *E. coli* 0111:B4 LPS at 1 ng/ml for 10 min at 23° C., added to whole blood containing heparin at 2 I.U/ml and the TNF-α concentrations determined after incubation for 4 h at 37° C. Each value is the mean of triplicate experiments. Controls only contained LPS.

In addition, the LPS-neutralizing activity of selected synthetic peptides of the invention were compared in a more complex environment of whole blood ex vivo to determine the effect of physiological concentrations of blood components such as plasma proteins, blood cells etc. on the detoxification efficacy. In pre-incubation experiments, concentrations of synthetic peptides, control peptide or PmB from 1 to 10 µg/ml were pre-incubated with 1 ng/ml E. coli 0111:B4 LPS in pyrogen-free saline for 30 min at 23° C., added to venous blood containing heparin at 2 I.U/ml as anti-coagulant and incubated for 4 h at 37° C. TNF-α concentrations were determined in appropriately diluted cell-free supernatants as described before. The results show (FIG. 11) almost complete inhibition of TNF-α production by the synthetic peptides BP1, BP2 or the control peptide $BPI_{(85-102)}$ as well as PmB even at the lowest concentration used of 1 µg/ml, essentially similar to the results obtained from the experiments with 10-fold diluted whole blood. The BP2.1 or BP2.2 peptide analogues, although approximately 80% and 70% homologous to the parent BP2 peptide, respectively, showed no significant reduction of TNF-α synthesis and were therefore not effective in detoxification of endotoxin under these conditions. This indicates that additional properties of synthetic peptides other than endotoxin binding are essential for LPS neutralization in a complex environment such as whole blood.

Figure 12:
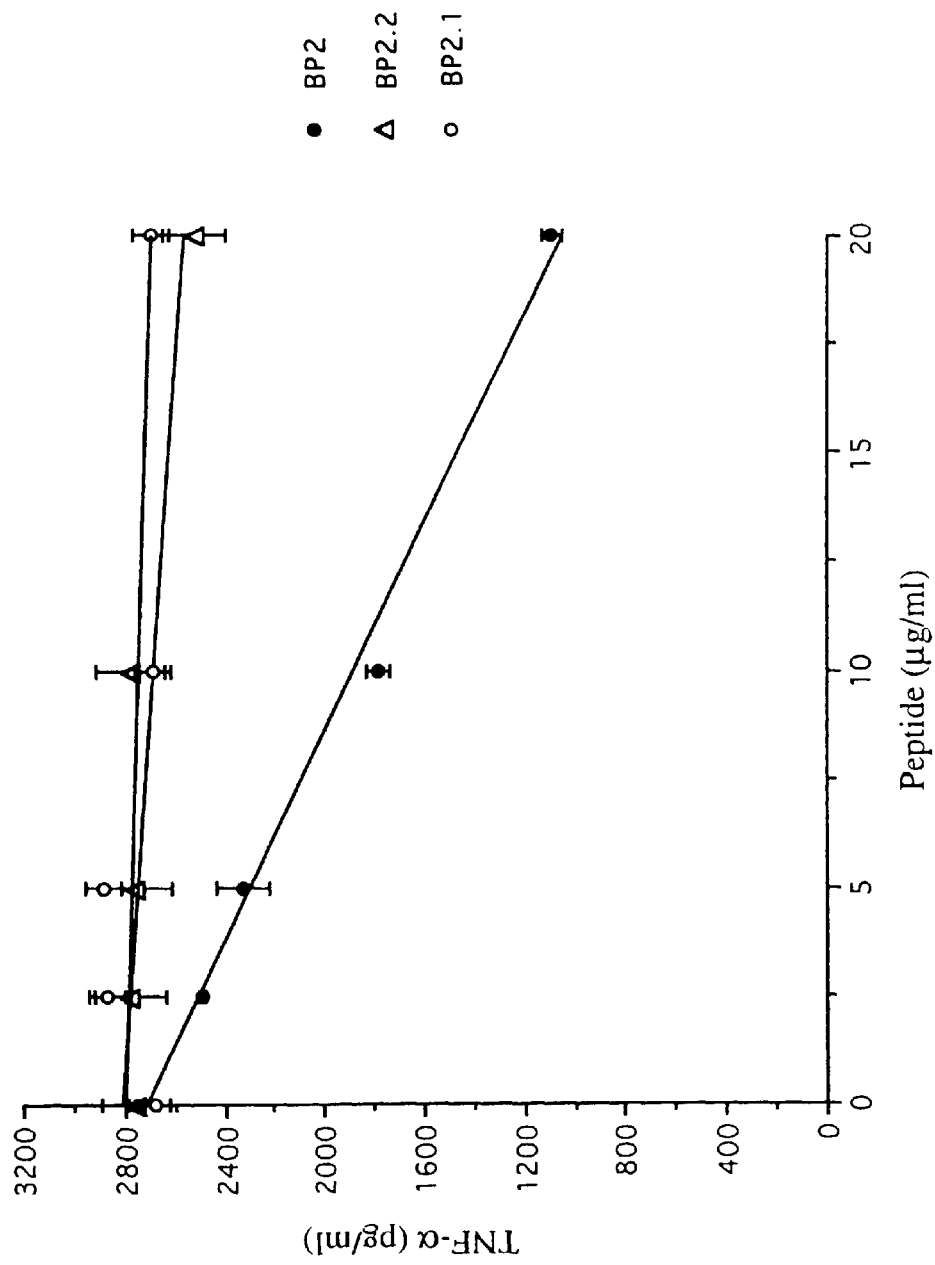
FIG. 12. Effect of pre-challenge addition of synthetic peptides on TNF-a levels induced by *E. coli* 0111:B4 LPS in whole blood ex vivo. The synthetic peptides BP2, BP2.1 or BP2.2 were added to whole blood containing heparin at 2 I.U/ml at the concentrations indicated and incubated for 10 min at 37° C. TNF-α concentrations were measured after incubation for 4 h at 37° C. subsequent to addition of *E. coli* 0111:B4 LPS at 1 ng/ml. The values represent the means of triplicate experiments. Controls only contained added LPS.

To determine whether addition of synthetic peptide to whole blood ex vivo prior to endotoxin challenge was effective in endotoxin neutralization assayed in terms of cytokine production, a synthetic peptide of the invention BP2, and the analogues BP2.1 or BP2.2 were added at concentrations of 2.5 to 20 µg/ml to whole blood and incubated for 10 min at 37° C. prior to the addition of 1 ng/ml *E. coli* 0111:B4 LPS. TNF-α concentrations were determined as previously described. Results show a dose-dependent inhibition of TNF-α production only by the BP2 synthetic peptide according to the invention, giving 57% inhibition of cytokine production at a peptide concentration of 20 µg/ml (FIG. 12). The structurally related LPS-binding synthetic peptide analogues BP2.1 and BP2.2 were ineffective in endotoxin neutralization under these conditions.

In vivo Detoxification

Figure 13:
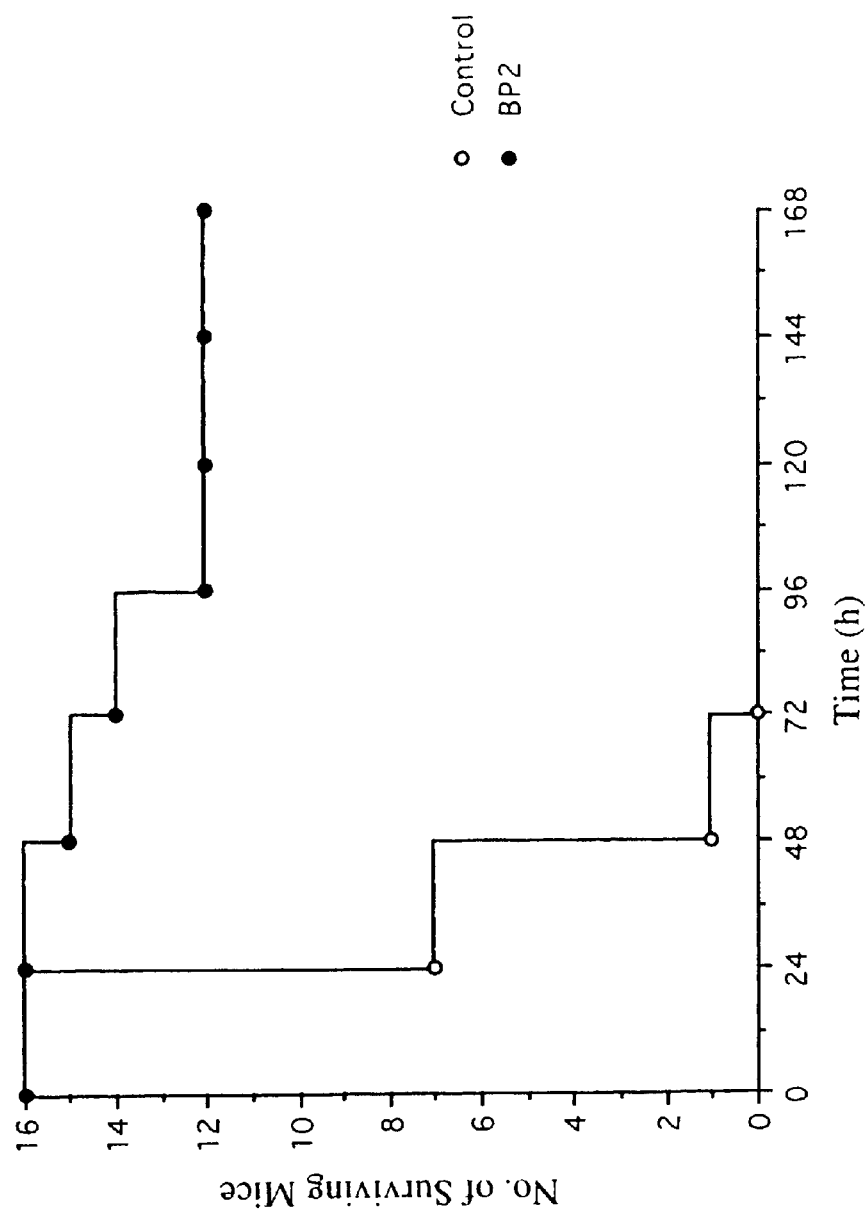
FIG. 13. Efficacy of synthetic peptide BP2 on survival in a murine model of lethal endotoxemia. Outbred femal Swiss-Webster mice of 7 to 8 weeks, weighing 28 to 30 g were treated with BP2 peptide by intraperitoneal (i.p) administration of a dose of 5 mg/Kg in pyrogen-free saline. Twenty minutes later the mice were challenged by i.p administration of the sensitizing agent Actinomycin D at 800

The efficacy of the peptides of the invention in the protection of experimental animals against the toxic effects of LPS or live pathogenic bacteria was investigated with the use of murine models of lethal endotoxemia and peritonitis Laboratory mice, which are normally tolerant to high doses of endotoxin and require a lethal dose ($LD_{100}$) of approximately 1 mg, may be sensitized with Actinomycin D to 10,000×lower amounts of endotoxin for lethality. In the present model, a dose of 100 ng of purified LPS from *E. coli* 0111:B4 LPS per sensitized animal was found to produce a lethality of 100% within 24 to 72 h. Preliminary experiments indicated that the synthetic peptide BP2 when administered intraperitoneally (i.p) in pyrogen-free (p.f) saline to an outbred Swiss strain of mice at dosages of 2.5 and 5 mg/Kg body weight was well tolerated with no adverse effects during a 2 week period of observation. In a series of experiments, groups of 4 to 6 Swiss mice 7 to 8 weeks old, weighing 28 to 30 g were treated with the synthetic peptide BP2 solubilized in p.f saline by i.p injection at a dosage of 5 mg/kg body weight. Twenty minutes later, the mice were challenged by i.p administration of Actinomycin D at 800 µg/Kg plus *E. coli* 0111:B4 LPS at 5 µg/Kg. The negative control groups only received Actinomycin D plus endotoxin. The survival of the treated animals was recorded at 24 h intervals during a seven day period of observation and compared with the control groups. The combined results of three independent experiments show 0% survival in the control groups at 72 h and a 75% survival at 7 days after treatment with the synthetic peptide of the invention (FIG. 13). Efficacy of peptides of the invention in the treatment of peritonitis in experimental animals was investigated using the clinically relevant pathogenic *Escherichia coli* strain 018:K1:H7 Bort. In a second series of experiments, groups of 6 to 8 outbred Swiss-Webster mice 7 to 8 weeks old were challenged by i.p injection of a predetermined lethal dose of live bacteria ($10^4$ CFU) in 0.5 ml pyrogen-free saline. After a delay of 1 h, treated groups received synthetic BP2 peptide in 0.5 ml p.f. saline at a dosage of 100 µg/mouse (4 mg/kg) and negative control groups only saline. The survival of the animals was recorded at 12 or 24 h intervals during a 7 day period of observation and compared with the control groups. The combined results of two independent experiments show 7% survival in the control groups after 3 days compared to 78.5% survival at 7 days after treatment with the synthetic peptide of the invention (FIG. 14). The peptides of the invention therefore provided a safe and effective protection of a highly significant number of experimental animals against the lethal effects of endotoxemia or peritonitis.

The invention is not merely directed at the novel peptides but also at pharmaceutical compositions comprising such a peptide or a combination of such peptides as active component. A pharmaceutical composition must further comprise said peptide in a form suitable for application to a mammal. This means it should be sterile and free of toxic components or contaminants. It can be in solution or any other dosage form suitable for pharmaceutical application. The dosage form and the composition of the pharmaceutical composition i.e. the presence of additives common to pharmaceutical applications of the nature envisaged are clear to a person skilled in the art for analogous applications with peptides as active component. A pharmaceutically acceptable carrier is required. The pharmaceutical composition according to the invention can be for treating one or more of topical or systemic microbial or parasitic infections, topical or systemic tumors, inflammation or septic shock.

The composition can be suitable for treatment of infection caused by an organism or compound of an organism, said organism being selected from the group comprising a bacterium, a fungus, a virus or a parasite. Specifically as is clear from the example a pharmaceutical composition is envisaged for treating an infection caused by a bacterium. Numerous bacterial type infections can be treated such as those caused by a bacterium exhibiting multiple drug resistance (MDR). Another suitable bacterial type infection can be treated such as that caused by a Gram positive bacterium. Infections caused by a Gram negative bacterium can also be treated with a pharmaceutical composition according to the invention. The invention also covers a pharmaceutical composition for treatment of infection caused by a parasite such as the parasite causing malaria or Trypanosomiosis. A pharmaceutical composition according to the invention can comprise a mixture of equimolar amounts of at least two peptides of the invention preferably of the same molecular weight. The pharmaceutical composition according to the invention can comprise at least one peptide of the invention and an antibiotic from the class consisting of penicillins, cephalosporins, β-lactams, aminoglycosides, quinolones, tetracyclines, macrolides, glycopeptides or lipopeptides, hydrophobic antibiotics, ribosome inhibitors or antibiotics having a large lipid-like lactone ring or derivatives or analogues thereof. The peptide and the antibiotic may be administered in amounts effective to treat infections caused by multiple-drug-resistant bacteria. The peptide and antibiotic may act synergistically.

The treatment for which the pharmaceutical composition is used can be curative or prophylactic. This will depend on the stage in which the patient is given the composition.

Methods of treatment are also covered by the scope of the invention. Such a method can comprise treatment of a mammal including a human, comprising application of a pharmaceutical composition according to the invention in a manner known per se for applying a peptide comprising pharmaceutical composition to said mammal for any of the purposes defined for the pharmaceutical composition as such or in combination. The treatment can be applied after trauma or suspected infection has or can have occurred. The treatment can suitably be applied after surgery.

Also belonging to the invention are methods of diagnosis e.g. comprising determining the presence of endotoxin in a sample of body matter of a mammal using a peptide according to the invention in a manner known per se in an assay capable of detecting degree of binding to Lipid A. Such an assay is illustrated in the examples and can be a solid state Lipid A binding assay. Another suitable embodiment comprises contacting a sample of body matter of a mammal with a peptide according to the invention and assessing whether complex formation between said matter and the peptide occurs and optionally determining how much complex formation occurs in a manner known per se. Such an assay is illustrated in the examples and can be a solid state Endotoxin Inhibition Lipid A binding assay. A method according to the invention is preferred, wherein the sensitivity is higher than obtainable with the Limulus assay on said sample. The sensitivity is preferably such that a detection level of 10 pg/ml in plasma is achieved. A sensitivity such that a detection level of <0.1 pg/ml in plasma is achieved is now obtainable.

Another application of the invention lies in a method for removal of endotoxin from a sample, comprising contacting said sample with a peptide according to the invention and removing the resulting complex of endotoxin and peptide in a manner known per se, such as an assay with immobilised peptide. In a preferred embodiment the endotoxin can be removed to a substantial level. Substantial implies more than 95%, preferably more than 98%.

A method for removal of LPS from a sample, comprising contacting said sample with a peptide according to the invention and removing the resulting complex of LPS and peptide in a manner known per se, such as an assay with immobilised peptide is also envisaged.

The treatment methods and other methods according to the invention as disclosed above can be carried out on samples derived from or consisting of donor material for transplant or implant. Obviously blood and plasma samples can be treated in such a manner to great advantage.

References

Ammons et al., 1994. Protective effects of an N-terminal fragment of bactericidal/permeability increasing protein in rodent models: role of bactericidal properties. J. Infect. Dis. 170, 1473–1482

Andreu et al., 1992. Shortened cecropin A-melittin hybrids. FEBS Lett. 296,190–194

Appelmelk et al. 1995. Diversity in lipid A binding ligands: comparison of lipid A and monoclonal antibodies with rBPI$_{23}$. Prog. Clin. Biol. Res. 392, 453–463

Arditi et al., 1994. Bactericidal/permeability-increasing protein protects vascular endothelial cells from lipopolysaccharide-induced activation and injury. Infect. Immun. 62, 3930–3936

Battafarano et al., 1995. Peptide derivatives of three distinct lipopolysaccharide binding proteins inhibit tumor necrosis factor-alpha secretion in vitro. Surgery 118, 318–324

Bessalle et al., 1993. Structure-function studies of amphiphilic antibacterial peptides. J. Med. Chem. 36, 1203–1209

Bhakdi et al., 1991. Stimulation of monokine production by lipoteichoic acids. Infect. Immun. 59, 4614–4620

Blackburn et al. 1991. Electrochemiluminescence detection for development of immunoassays and DNA probe assays for clinical diagnostics. Clin. Chem. 37, 1534–1539

Blondelle et al., 1992. Design of model amphipathic peptides having potent antimicrobial activities. Biochemistry. 31, 12688–12694

Boman et al., 1989. Antibacterial and antimalarial properties of peptides that are cecropin-melittin hybrids. FEBS Lett. 259, 103–106

Boman, 1995. Peptide antibiotics and their role in innate immunity. Annu. Rev. Immunol. 13, 61–92

Brade et al., 1990. A 28 kDa protein of normal mouse serum binds lipopolysaccharide of gram-negative and lipoteichoic acids of gram-positive bacteria. Microb. Pathog. 9, 355–362

Capodici et al., 1994. Effect of lipopolysaccharide (LPS) chain-length on interactions of bactericidal/permeability-increasing protein and its bioactive 23-kilodalton NH2-terminal fragment with isolated LPS and intact Proteus mirabilis and *Escherichia coli*. Infect. Immun. 62, 259–265

Cardin et al. 1989. Molecular modeling of protein-glycosaminoglycan interactions. Arteriosclerosis 9, 21–31

Cuervo et al., 1988. The magainins: Sequence factors relevant to increased anti-microbial activity and decreased hemolytic activity. Pep. Res. 1, 81–86

Dokter et al., 1994. G(Anh) tetra, a natural bacterial cell wall breakdown product, induces interleukin-1α and interleukin-6 expression. J. B. C 269, 4201–4206

Evans et al., 1995. Protective effects of a recombinant amino-terminal fragment of human bactericidal/permeability-increasing protein in an animal model of gram-negative sepsis. J. Infect. Dis. 171, 153–160

Fink et al., 1989. Design, synthesis and antibacterial activity of cecropin-like model peptides. Int. J. Peptide Protein Res. 33, 412–421

Freudenberg et al., 1991. Tumor necrosis factor alpha mediates lethal activity of killed gram-negative and gram-positive bacteria in D-galactosamine-treated mice. Infect. Immun. 59,2110–2115

Gray et al., 1994. Bactericidal activity of synthetic peptides based on the structure of the 55-kilodalton bactericidal protein from human neutrophils. Infect. Immun. 62, 2732–2739

Heuman et al., 1994. Gram-positive cell walls stimulate synthesis of tumor necrosis factor alpha and interleukin-6 by human monocytes. Infect. Immun. 62, 2715–2721

Hoess et al. 1993. Crystal structure of an endotoxin-neutralizing protein from the horseshoe crab Limulus anti-LPS factor at 1.5 Å resolution. EMBO J. 12, 3351–3356

Iwata et al., 1994. Design and synthesis of amnphipathic $3_{10}$-helical peptides and their interactions with phospholipid bilayers and ion-channel formation. J. Biol. Chem. 269, 4928–4933

Kloczewiak et al., 1994. Synthetic peptides that mimic the binding site of Horseshoe crab anti-lipopolysaccharide factor. J. Infect. Dis. 170, 1490–1497

Kohn et al., 1993. Protective effect of a recombinant amino-terminal fragment of bactericidal/permeability-increasing protein in experimental endotoxemia. J. Infect. Dis. 168, 1307–1310

Larrick et al., 1993. Antimicrobial activity of rabbit CAP18-derived peptides.
Antimicrob. Agents Chemother. 37, 2534–2539

Lee et al., 1989. Antibacterial peptides from pig intestine: Isolation of a mammalian cecropin. Proc. Natl. Acad. Sci. USA. 86, 9159–9162

Leeson et al., 1994. Evidence for lipopolysaccharide as the predominant proinflammatory mediator in sup ematants of antibiotic-treated bacteria. Infect. limun. 62, 4975–4980

Little et al., 1994. Functional domains of recombinant bactericidal/permeability-increasing protein (rBPI$_{23}$). J. Biol. Chem. 21, 1865–1872

Novitsky et al., 1994. Limulus amoebocyte lysate (LAL) detection of endotoxin in human blood. J. Endotox. Res. 1, 253–263

Pieroni et al., 1970. A simple method for quantitation of submicrogram amounts of bacterial endotoxin. Proc. Soc. Exp. Biol. Med. 133, 790–794

Piers et al., 1994. Improvement of outer membrane permeability and lipopolysaccharide-binding activities of an antimicrobial cationic peptide by C-terminal modification. Antimicrob. Agents Chemother. 38, 2311–2316

Rustici et al., 1993. Molecular mapping and detoxification of the lipid A binding site by synthetic peptides. Science 259, 361–365

Saberwal et al., 1994. Cell-lytic and antibacterial peptides that act by perturbing the barrier function of membranes: facets of their conformational features, structure-function correlations and membrane-perturbing abilities. Biochim. Biophys. Acta. 1197, 109–131

Storici et al., 1994. Chemical synthesis and biological activity of a novel antibacterial peptide deduced from pig myeloid cDNA. FEBS Lett. 337, 303–307

Tossi et al., 1994. Identification and characterization of a primary antibacterial domain in CAP18, a lipopolysaccharide binding protein from rabbit leukocytes. FEBS Lett. 339, 108–112

Wade et al., 1990. All D-containing amino acid containing channel-forming antibiotic peptides. Proc. Natl. Acad. Sci. USA. 87, 4761–4765

Weiss et al., 1992. Human bactericidal/permeability-increasing protein and a recombinant $NH_2$-terminal fragment cause killing of serum-resistant gram-negative bacteria in whole blood and inhibit tumor necrosis factor release induced by the bacteria. J Clin. Invest. 90, 1122–1130

The contents of the cited references are to be considered incorporated herein in their totality.

TABLE 1

Bactericidal activities of the synthetic and control peptides towards representative Gram-negative and Gram-positive bacteria

| Peptide | Concentration effective dose $(M^{-6})$ | % bacteria killed |
|---|---|---|
| Bactericidal activity towards $10^7$ E. coli 0111:B4 bacteria/ml LB medium at 37° C. | | |
| BP1 | 3 | 88 |
| BP2 | 3 | 91 |
| $BPI_{(85-102)}$ | 3 | 31 |
| Bactericidal activity towards $10^7$ S. aureus bacteria/ml LB medium 37° C. | | |
| BP1 | 3 | 34 |
| BP2 | 3 | 55 |
| $BPI_{(85-102)}$ | 3 | 0 |

---

We claim:

1. An isolated peptide comprising at least 12 amino acids, wherein the peptide is amphipathic, cationic and forms a stable α-helix, and is represented by the following formula (I) or the retro orientation of formula (I):

   (I)

wherein $R^1$, $R^2$, and $R_3$ are each an amino acid, and a, b and c are each independently an integer from 0 to 15, wherein each $R^1$ for each value of a, each $R^2$ for each value of b and each $R^3$ for each value of c are independently the same or different, wherein the combination of a+b is not greater than 15, each A is an amino acid independently selected from the group consisting of Lys, Arg, and His, each B is an amino acid independently selected from the group consisting of Phe, Trp, and Tyr, each C is an amino acid independently selected from the group consisting of Leu, Ile, Val and Ala, X is (A-B-C-A) or (A-C-B-A), and m is an integer from 2 to 8, wherein each X for each value of m is independently the same or different, and n is an integer from 1 to 3.

2. The isolated peptide according to claim 1, wherein a+b and c are each an integer of from 1 to 10.

3. The isolated peptide according to claim 1, wherein $R^1_a$ is selected from the group consisting of:

$Gly_p$, wherein p is an integer of from 1 to 10; and $Ala_q$, wherein q is an integer of from 1 to 10.

4. The isolated peptide according to claim 1, wherein $R^1$, $R^2$, and $R^3$ do not comprise an amino acid selected from the group consisting of A, B, C as defined in claim 1.

5. The isolated peptide according to claim 1, wherein motifs (A-C-B-A) are present in said peptide in a greater amount than motifs (A-B-C-A).

6. The isolated peptide according to claim 1, wherein n=3.

7. An isolated peptide comprising SEQ ID NO:1.

8. An isolated peptide comprising SEQ ID NO:2.

9. An isolated peptide comprising SEQ ID NO:3.

10. An isolated peptide comprising SEQ ID NO:4.

11. An isolated peptide comprising SEQ ID NO:5.

12. The isolated peptide according to claim 1, wherein the peptide is coupled to a non-peptide carrier, radioactive tag or fluorescent label.

13. A pharmaceutical composition comprising the isolated peptide according to claim 1 as an active component for treating microbial infection and a pharmaceutically acceptable carrier in a pharmaceutically acceptable dosage form.

14. The pharmaceutical composition according to claim 13, wherein the infection is caused by an organism or a compound of an organism, said organism being selected from the group consisting of a bacterium, a fungus, a virus and a parasite.

15. The pharmaceutical composition according to claim 13, wherein the infection is caused by a bacterium.

16. The pharmaceutical composition according to claim 13, wherein the infection is caused by a bacterium exhibiting multiple drug resistance (MDR).

17. The pharmaceutical composition according to claim 13, wherein the infection is caused by a Gram positive bacterium.

18. The pharmaceutical composition according to claim 13, wherein the infection is caused by a Gram negative bacterium.

19. A pharmaceutical composition comprising a mixture of at least two isolated peptides according to claim 1 as active components for treating topical and systemic microbial or parasite infections, or both, and a pharmaceutically acceptable carrier in a pharmaceutically acceptable dosage form.

20. The pharmaceutical composition according to claim 13, further comprising an antibiotic selected from the group consisting of penicillins, cephalosporins, β-lactams, aminoglycosides, quinolones, tetracyclines, macrolides, glycopeptides or lipopeptides, ribosome inhibitors or antibiotics having a large lipid-like lactone ring.

21. The pharmaceutical composition according to claim 13, wherein the infection is caused by a parasite.

22. A pharmaceutical composition comprising an isolated peptide according to claim 1 as active component for treating septic shock.

23. The pharmaceutical composition according to claim 13, wherein the treatment is prophylactic.

24. A method for treatment of microbial infection in a mammal, comprising administering to a mammal in need of such treatment an amount of the isolated peptide according to claim 1 effective to reduce infection.

25. The method according to claim 24, wherein said treatment is applied after trauma or suspected infection has occurred.

26. The method according to claim 24, wherein said treatment is applied after surgery.

27. A pharmaceutical composition for treating bacterial inflammation comprising a therapeutically effective amount of an isolated peptide according to claim 1, and a pharmaceutically acceptable carrier.

28. The isolated peptide according to claim 1, wherein a+b and c are each 0.

29. The pharmaceutical composition according to claim 21, wherein said parasite is selected from the group consisting of a parasite causing malaria and a parasite causing Trypanosomiosis.

30. A method for treatment of microbial infection in a human, comprising administering to a human in need of such treatment an amount of the isolated peptide according to claim 1 effective to reduce infection.

31. A method for inhibiting the growth of a microbe, comprising the step of contacting a microbe with an amount of the isolated peptide according to claim 1 effective to inhibit the growth of a microbe.

32. A method for inhibiting the growth of a Gram-negative bacterium, comprising the step of contacting a Gram-negative bacterium with an amount of the isolated peptide according to claim 1 effective to inhibit the growth of a Gram-negative bacterium.

33. A method for inhibiting the growth of a Gram-positive bacterium, comprising the step of contacting a Gram-positive bacterium with an amount of the isolated peptide according to claim 1 effective to inhibit the growth of a Gram-positive bacterium.

34. The isolated peptide according to claim 1, wherein $R^2_b$ is ACAA, wherein each A and C is as independently defined in claim 1.

35. The pharmaceutical composition according to claim 13, wherein said isolated peptide is present in said composition in an amount effective to treat one or more of the conditions selected from the group consisting of a topical microbial infection, a topical parasitic infection, a systemic microbial infection, a systemic parasitic infection, a topical tumor, a systemic tumor, inflammation and bacterial septic shock.

36. The pharmaceutical composition according to claim 13, wherein said composition is in the form of a topical preparation, a parenteral preparation or an oral preparation.

* * * * *